US011021750B2

(12) United States Patent
Baird et al.

(10) Patent No.: US 11,021,750 B2
(45) Date of Patent: Jun. 1, 2021

(54) BIOMARKERS FOR PREDICTING RISK OF ACUTE ISCHEMIC STROKE AND METHODS OF USE THEREOF

(71) Applicant: The Research Foundation for State University of New York, Albany, NY (US)

(72) Inventors: Alison E. Baird, Brooklyn, NY (US); Mateusz Adamski, Kradow (PL)

(73) Assignee: THE RESEARCH FOUNDATION FOR STATE UNIVERSITY OF NEWYORK, Albany, NY (US)

( * ) Notice: Subject to any disclaimer, the term of this patent is extended or adjusted under 35 U.S.C. 154(b) by 0 days.

(21) Appl. No.: 15/028,732

(22) PCT Filed: Oct. 14, 2014

(86) PCT No.: PCT/US2014/060532
§ 371 (c)(1),
(2) Date: Apr. 12, 2016

(87) PCT Pub. No.: WO2015/054700
PCT Pub. Date: Apr. 16, 2015

(65) Prior Publication Data
US 2016/0258019 A1    Sep. 8, 2016

Related U.S. Application Data

(60) Provisional application No. 61/890,274, filed on Oct. 13, 2013.

(51) Int. Cl.
| | |
|---|---|
| C12Q 1/68 | (2018.01) |
| C12Q 1/6883 | (2018.01) |
| C12Q 1/686 | (2018.01) |
| C12Q 1/6851 | (2018.01) |

(52) U.S. Cl.
CPC ........... *C12Q 1/6883* (2013.01); *C12Q 1/686* (2013.01); *C12Q 1/6851* (2013.01); *C12Q 2600/158* (2013.01)

(58) Field of Classification Search
None
See application file for complete search history.

(56) References Cited

U.S. PATENT DOCUMENTS

| | | | | |
|---|---|---|---|---|
| 7,749,700 B2 * | 7/2010 | Baird | ................... | C12Q 1/6883 435/287.1 |
| 2007/0005261 A1 | 1/2007 | Serena et al. | | |
| 2010/0267582 A1 * | 10/2010 | Baird et al. | ............. | C40B 30/04 506/9 |
| 2011/0008779 A1 | 1/2011 | Liew | | |

OTHER PUBLICATIONS

Adamski et al. (Journal of Biomolecular Screening 18(9)1008-1017) (Year: 2013).*
Supplemental materials from : Adamski et al. Journal of Biomolecular Screening 18(9)1008-1017, 4 pages (Year: 2013).*
Leong et al. (Biomaterials 28 (2007) 203-210) (Year: 2007).*
Devonshire Methods 59 (2013) 89-100 (Year: 2013).*
Adamski, Mateusz G et al., "Next-Generation qPCR for the High-Throughput Measurement of Gene Expression in Multiple Leukocyte Subsets", Journal of Biomolecular Screening, 18(9): 1008-1017 (2013).
Bustin, Stephen A. et al., "The MIQE Guidelines: Minimum Information for Publication of Quantitative Real-Time PCR Experiments", Clinical Chemistry, 55: 611-622 (2009).
Chang, Tai-Jay et al., "Up-regulation of B-actin, cyclophilin and GAPDH in N1S1 rat hepatoma", Oncology Reports, 5: 469-471 (1998).
Devonshire, Alison S. et al., "Application of next generation qPCR and sequencing platforms to mRNA biomarkers analysis", Methods, 59: 89-100 (2013).
Dheda, Keertan et al., "Validation of housekeeping genes for normalizing RNA expression in real-time PCR", BioTechniques, 37(1): 112-119 (2004).
Feroze-Merzoug, F. et al., Peptidylprolyllsomerase A (PPIA) as a Preferred International Control Over GAPDH and B-Actin in Quantitative RNA Analyses, BioTechniques, 32(4): 776-782 (2002).
Li, Rena et al., "An old method facting a new challenge: re-visiting housekeeping proteins as internal reference control for neuroscience research", Life Sci., 92(13): 747-751 (2013).
Lin, Juntang et al., "Histological evidence: housekeeping genes beta-actin and GAPDH are of limited value for normalization of gene expression", Dev. Genes Evol., 222: 369-376 (2012).
Liu, Meile et al., "Progress Curve Analysis of qRT-PCR Reactions Using the Logistic Growth Equation", Biotechnol. Prog., 27: 1407-1414 (2011).
Livak, Kenneth J. et al., Analysis of Relative Gene Expression Data Using Real-Time Quantitative PCR and the 2-Method, Methods, 25: 402-408 (2001).
Nishimura, Masuhiro et al., "Effects of Dimethyl Sulphoxide and Dexamethasone on mRNA Expression of Myogenesis- and Muscle Proteolytic System-related Genes in Mouse Myoblastic C2C12 Cells", J. Biochem., 144(6): 717-724 (2008).
Pfaffl, Michael W., "A new mathematical model for relative quantification in real-time RT-PCR", Nucleic Acids Research, 29(9): 2002-2007 (2001).
Sikand, Kavleen et al., "Housekeeping Gene Selection Advisory: Glyceraldehyde-3-Phosphate Dehydrogenase (GAPDH) and B-Actin Are Targets of miR-644a", PLoS ONE, 7(10): e47510 (2012).
Spurgeon, Sandra L. et al., "HighThroughput Gene Expression Measurement with Real Time PCR in a Microfluidic Dynamic Array", PLoS ONE, 3(2): e1662 (2008).
Vandesompele, Jo et al., "Accurate normalization of real-time quantitative RT-PCR data by geometric averaging of multiple internal control genes", Genome Biology, 3(7) (2002).

(Continued)

*Primary Examiner* — Juliet C Switzer
(74) *Attorney, Agent, or Firm* — Kathleen D. Rigaut; Howson & Howson LLP

(57) ABSTRACT

Biomarkers useful for the diagnosis and treatment of acute ischemic stroke are disclosed. Also provided is a quantitative assay method for accurately identifying transcript number in a biological sample.

2 Claims, 5 Drawing Sheets
(4 of 5 Drawing Sheet(s) Filed in Color)
Specification includes a Sequence Listing.

(56) References Cited

OTHER PUBLICATIONS

International Search Report/Written Opinion, dated Apr. 30, 2015, issued in corresponding International Application No. PCT/US2014/060532, filed Oct. 14, 2014.

* cited by examiner

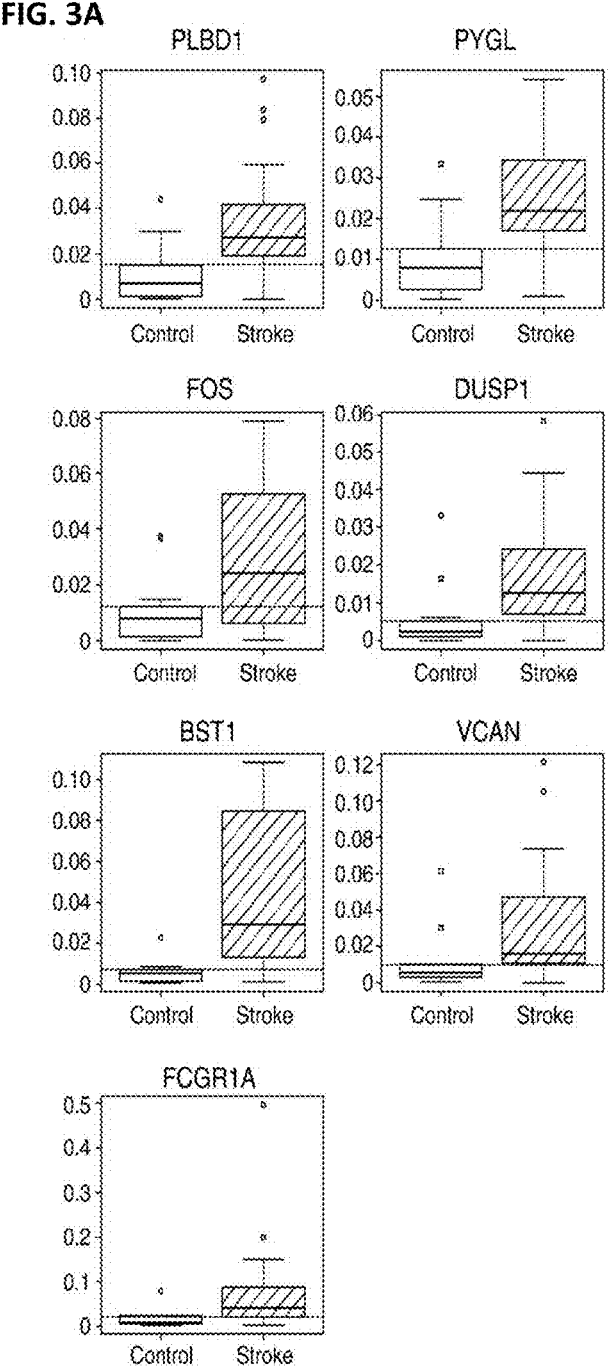
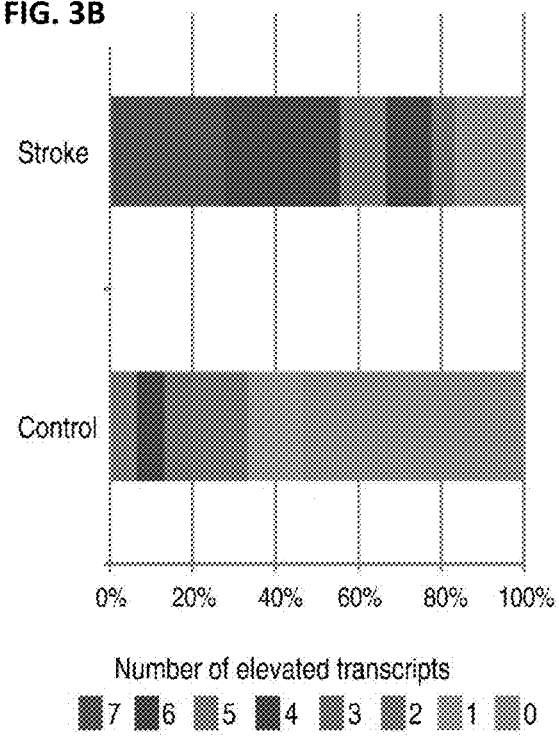
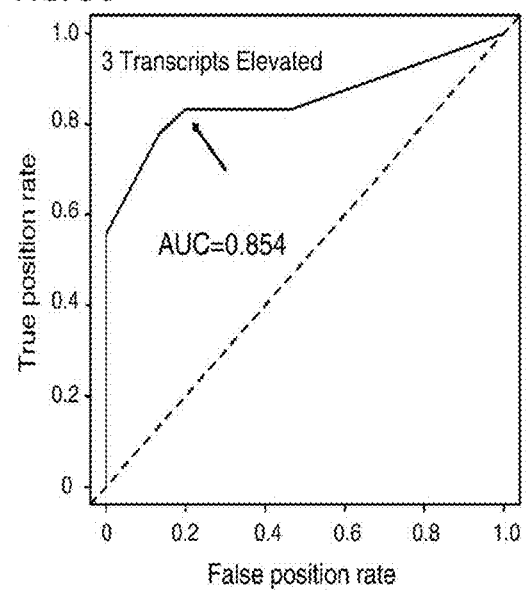

BIOMARKERS FOR PREDICTING RISK OF ACUTE ISCHEMIC STROKE AND METHODS OF USE THEREOF

This application claims priority to U.S. Provisional Application No. 61/890,274 filed Oct. 13, 2013, the entire contents being incorporated herein by reference as though set forth in full.

Pursuant to 35 U.S.C. § 202(c) it is acknowledged that the U.S. Government has rights in the invention described, which was made with funds from the National Institutes of Health, Grant Number, ROI EB010087.

FIELD OF THE INVENTION

This invention relates to the fields of cardiovascular disease, ischemic stroke and biomarker detection. More specifically, the invention discloses biomarkers that are present in peripheral blood which are indicative of an increased risk for ischemic stroke and methods of use thereof in diagnostic and prognostic assays. Also disclosed are screening assays utilizing the biomarkers of the invention to identify agents useful for the treatment and prevention of ischemic stroke.

BACKGROUND OF THE INVENTION

Several publications and patent documents are cited throughout the specification in order to describe the state of the art to which this invention pertains. Each of these citations is incorporated herein by reference as though set forth in full.

Strokes result from focal reductions of blood flow to the brain and are second to coronary heart disease (CHD) in terms of vascular disease incidence, morbidity, and mortality. Currently, there are about 795,000 new and recurrent strokes per year in the U.S. compared with 1,350,000 new and recurrent coronary events. There is a substantial additional burden of asymptomatic cerebrovascular disease. About 83% of strokes are due to arterial vascular occlusion (ischemic stroke), and about 17% are due to vascular rupture (hemorrhagic stroke).

Many scientific advances have occurred in stroke diagnosis, treatment, and prevention over the past 10 to 20 years, such as advances in neurovascular imaging and intravenous tissue plasminogen activator therapy, but important questions remain unanswered. Modifiable risk factors account for only about 60% of the population-attributable risk (PAR) for stroke (9-10), as opposed to risk factors identified for CHD, which may account for more than 90% of the attributable risk. The mechanisms for over 30% of ischemic strokes are not known, even after extensive workup.

Stroke diagnosis is inaccurate in up to 30% of patients acutely, and it is not possible to reliably distinguish between ischemic and hemorrhagic stroke clinically. No blood-based diagnostic marker has yet been developed for stroke, unlike for acute coronary syndromes; this might be because of issues related to the blood-brain barrier. There is also no reliable way to predict which patients will develop hemorrhagic transformation in the brain after thrombolytic therapy.

Clearly, a need exists in the art for a panel of biomarkers associated with an increased risk of stroke for the management and treatment thereof.

SUMMARY OF THE INVENTION

In accordance with the present invention, a method for identifying patients having an increased risk for the development of acute ischemic stroke is provided. An exemplary method entails obtaining a biological sample from a test subject and determining the expression levels of at least three gene markers from Table 4, wherein upregulation of said markers relative to predetermined control levels observed in non-afflicted controls, are indicative of an increased risk for the development of acute ischemic stroke. In one embodiment said three gene markers are PLBD1, PYGL2, and BST1. The method may further comprise analysis of DUSP1, VCAN, FCGR1A and FOS or DUSP1, FOS, NPL, KIAA0146 and ENTPD1. In yet another embodiment the gene markers consist of PILRA, BCL6, FPR1, LY96, S100A9, S100A12 and MMP9. The method may further comprise determination of expression levels of any of the markers listed in Table 4. In yet another aspect, expression levels of each of BST1, S100A9, PLBD1, S100A12, SUSP1, ETS2, S100P, FOS, CYBB, PYGL, F5, CD93, ENTPD1, CKAP4, ADM and IQGAP1 are determined. In a particularly preferred embodiment of the invention, the markers are PLBD1, PYGL2, BST1, DUSP1, VCAN, FCGR1A and FOS.

In certain aspects, the determining step comprises contacting said sample with an agent having affinity for said ischemic stroke associated markers, the agent forming a specific binding pair with said markers and further comprising a detectable label, measuring said detectable label, thereby determining expression level of said marker in said sample. In a particularly preferred embodiment, the expression levels are determined using the input quantity method described in Example II. The method may further comprises creating a report summarizing the data obtained by the determination of said ischemic stroke associated marker expression levels and may include recommendation for a treatment modality of said patient.

In yet another aspect of the invention, kits are provided for practicing the methods disclosed herein.

The invention also provides a method for identifying agents which useful for the treatment of acute ischemic stroke. An exemplary method comprises contacting a cell comprising one or more ischemic stroke associated markers from Table 4 with a test agent and assessing the effect of said agent on modulation of expression levels of said markers relative to untreated cells, agents which modulate expression of any of the markers in step a) having utility for the treatment of acute ischemic stroke.

In another embodiment, the invention provides a "test and treat" method for acute ischemic stroke. The patient is first assessed for the expression levels of the ischemic stroke associated markers described above, and if the marker profile is indicative of the presence or predisposition towards a stroke, the patient is administered treatment and placed on the appropriate therapeutic regimen.

A method for quantitative analysis of standard and high-throughput qPCR expression data based on input sample quantity is also disclosed. In one aspect the method comprises obtaining a biological sample for analysis of target gene expression from a test subject and a control subject and measuring input quantity of said samples and extracting RNA transcripts. The extracted RNA is then reverse transcribed into cDNA and the cDNA amplified via polymerase chain reaction. The amplification efficiency and correlation coefficients for each amplified transcript is then determined and relative fold changes between said test and control are calculated using $$\frac{T_C}{C_C} = \frac{ccC}{ccT} \times (1+E)^{(nCq,C-nCq,T)}$$

wherein, when cells are used as the biological sample, Tc is the number of transcripts per cell in said test subject, Cc is the number of transcripts per cell in a control subject, ccT is the input cell count for said test subject, ccC is the cell input for said control subject, E is the efficiency of target cDNA amplification, and nCq is the cycle number at which amplification crosses the threshold. The method can also comprise determining the absolute value differences between target gene transcripts in test subject and control subject, wherein efficiency of target cDNA amplification is known and said method further comprises introduction of a standard reference sample containing a known quantity of said transcripts, said absolute value difference being calculated using $$X_C = \frac{(1+E)^{(nCq,C-nCq,X)}}{ccX}.$$

In yet another aspect, the method can also comprise determining the absolute value differences between target gene transcripts in test subject and control subject, wherein efficiency of target cDNA amplification is unknown and said method further comprises introduction of a standard reference sample containing a known quantity of said transcripts, said absolute value difference being calculated using $$X_C = \frac{2^{(nCq,cDNA-nCq,X)}}{ccX}.$$

BRIEF DESCRIPTION OF THE DRAWING

The application file contains at least one drawing executed in color. Copies of this application with color drawings will be provided by the Patent and Trademark Office upon request and payment of the necessary fee.

FIG. 3 Characteristics of a 7 transcript classifier for ischemic stroke detection (A) Boxplots demonstrating the threshold values for defining elevated expression of each of the transcripts (PLBD1, PYGL, FOS, DUSP1, BST1, VCAN, FCGR1A). The threshold was set at above the third quartile value in the control group (dashed line on each boxplot). The threshold value was the normalized transcript copy number. (B) Bar graphs depicting the number of transcripts elevated in the stroke patients and the control subjects. In the stroke bar the value for the 7 transcript elevation represents the 5 stroke patients who had all 7 transcripts elevated, the value for 6 transcripts represents the 5 patients who had 6 transcripts elevated, the value for 5 transcripts elevated represents the one stroke patient who had 5 transcripts elevated, etc. In Cluster 1, 83% (15/18) of the stroke patients had 3 or more of the 7 transcripts elevated while 20% (3/15) of the control group showed elevation of 3 or more of the 7 transcripts. Hence the sensitivity was 83% and the specificity was 80%. (C) ROC Analysis for Cluster 1 for Stroke Classification revealed that the AUC was 0.854. Elevation of 3 or more transcripts gave the greatest sensitivity and specificity.

DETAILED DESCRIPTION OF THE INVENTION

Figure 1:
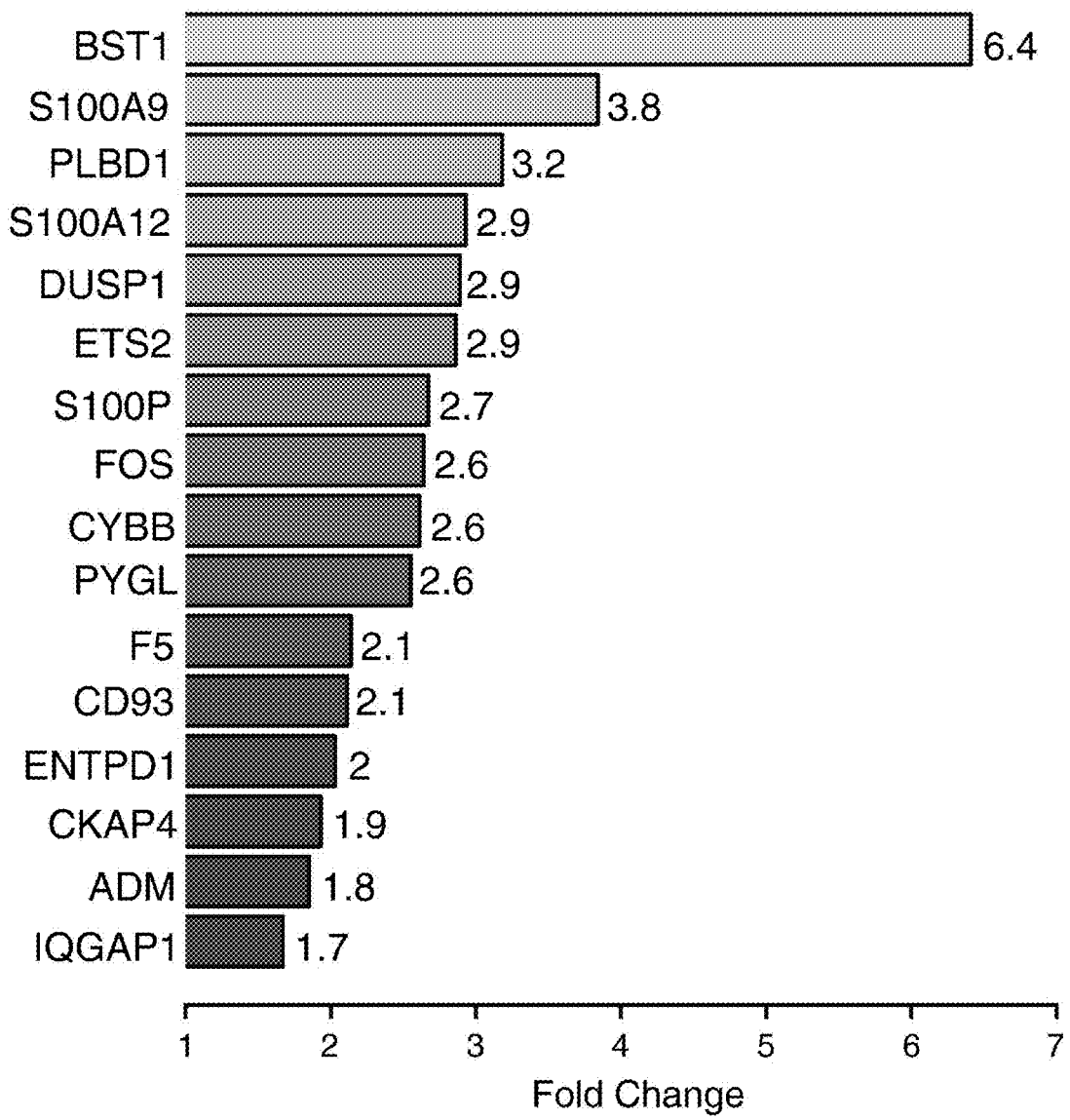
FIG. 1 shows stroke related transcripts fold changes with p<0.05. This bar graph shows the fold change levels for 16 up-regulated transcripts in ischemic stroke.

Stroke is a leading cause of death and disability in the community and new diagnostics and therapeutics are greatly needed. Inflammation and immune response after stroke impacts significantly on tissue and clinical outcome[2,3]. Application of molecular and cellular approaches to study the immune system in stroke may offer new diagnostic and therapeutic approaches.

Using microarrays that contained between 22,000 and 54,000 oligonucleotide probes, genomic profiling has been applied to the circulating leukocytes of human stroke patients[4-7]. Peripheral blood mononuclear cells (PBMCs) and whole blood samples[5,6] were used for these studies. In three independent analyses 22, 18 and 9 transcripts showed utility for stroke detection[4-6]. In these studies ribonucleic acid (RNA) was sampled between 3 and 72 hours after stroke onset. Different microarrays from two companies (Affymetrix and Illumina) were used and therefore signal intensity was assessed differently for each study. Despite these methodological and experimental differences there was some overlap among the transcripts identified and panels were able to be applied between the study cohorts [4-7].

These microarray studies raised the possibility of added diagnostic utility in stroke from genomic profiling of circulating leukocytes to clinical and neuroimaging information during the time window for thrombolytic therapy[8-11]. Expression changes were seen as early as 3 hours post stroke and persisted at 5 and 24 hours[5]. However, further translation and application of these microarray results has been hindered by data normalization issues, cost, high turnaround time and the limited availability of arrays. While providing unprecedented coverage of the transcriptome, microarray data are also limited by low sensitivity and low accuracy for transcripts expressed at low levels[12,13].

The majority of these stroke-related transcripts were not validated with standard quantitative polymerase chain reactions (qPCR)—the gold standard for measuring gene expression. qPCR-based approaches are more likely than microarrays to be applied and developed for rapid assays and automated point of care systems that would be needed for early stroke diagnosis[14,15]. Compared to microarrays qPCR approaches are characterized by shorter assay turnaround times and high sensitivity, with a theoretical limit of detection of a single copy of messenger ribonucleic acid (mRNA) target[16]. Until now standard reverse transcription (RT)-qPCR has been feasible for studying 6 genes at most from typical clinical samples.

Recently next generation microfluidic high throughput qPCR approaches have become available. These methods, known as high throughput RT-qPCR (HT RT-qPCR) or nanofluidic qPCR, permit the rapid quantification of multiple transcripts using small sample volumes[17,18] with very high sensitivity. Plates can contain up to 96 samples in which 96 transcripts can be simultaneously studied in 9,216 reactions. We have applied HT RT-qPCR to forty candidate markers identified in the three prior gene expression profiling studies to (1) quantitate individual transcript expression, (2) identify transcript clusters and (3) assess the clinical diagnostic utility of the clusters identified for ischemic stroke detection.

Using cluster analysis, we have discovered that groups of genes, ranging from 3 to 8 per cluster, containing individual transcripts from the 3 different panels give highly significant results in this small sample, with p values of the order of $10^{-11}$ (see Table 4 below). The genes cluster similarly, whether or not the subjects are clustered by stroke and control status. One aspect of the invention entails multiplexing the 3-8 transcripts for use in spFRET approaches.

The biomarkers of the invention include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides.

A "biomarker" is any gene or protein whose level of expression in a tissue or cell is altered compared to that of a normal or healthy cell or tissue. Biomarkers of the invention are selective for underlying risk of progression to ischemic stroke. By "selectively overexpressed in peripheral blood" is intended that the biomarker of interest is overexpressed in peripheral blood in stroke patients relative to levels observed in control patients. Thus, detection of the biomarkers of the invention permits the differentiation of samples indicative of increased risk of ischemic stroke. Biomarker profiles for this purpose are also within the scope of the invention.

As used herein, the term "risk" refers to an aspect of personal behavior, or lifestyle, an environmental exposure, or an inborn or inherited characteristic which on the basis of epidemiological evidence is known to be associated with health related condition(s) considered important to ameliorate or prevent.

The phrase "genetic signature" refers to a plurality of nucleic acid molecules whose expression levels are indicative of a given metabolic or pathological state. The genetic signatures described herein can be employed to characterize at the molecular level the biomarker profile that is associated with an increased risk of ischemic stroke, thus providing a useful molecular tool for predicting outcomes, for identifying patients at risk, and for use in biomarker in assays for evaluating ischemic stroke preventive agents.

For purposes of the present invention, "a" or "an" entity refers to one or more of that entity; for example, "a cDNA" refers to one or more cDNA or at least one cDNA. The terms "a" or "an," "one or more" and "at least one" can be used interchangeably herein. It is also noted that the terms "comprising," "including," and "having" can be used interchangeably. Furthermore, a compound "selected from the group consisting of" refers to one or more of the compounds in the list that follows, including mixtures (i.e. combinations) of two or more of the compounds. According to the present invention, an isolated, or biologically pure molecule is a compound that has been removed from its natural milieu. As such, "isolated" and Abiologically pure@ do not necessarily reflect the extent to which the compound has been purified. An isolated compound of the present invention can be obtained from its natural source, can be produced using laboratory synthetic techniques or can be produced by any such chemical synthetic route. The term "genetic alteration" as used herein refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

"Sample" or "patient sample" or "biological sample" generally refers to a sample which may be tested for a particular molecule, preferably a genetic signature specific marker molecule, such as a marker shown in the tables provided below. Samples may include but are not limited to peripheral blood cells, CNS fluids, serum, plasma, buccal swabs, urine, saliva, tears, pleural fluid and the like.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated. Thus, the term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest.

The phrase "input sample quantity" refers to accurate measurement of the amount of the starting material used for extraction of RNA. For example, for cell suspensions, cell counts are performed; for solid tissues, tissue volume is determined.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any specific marker gene or nucleic acid, but does not hybridize to other human nucleotides. Also polynucleotide which "specifically hybridizes" may hybridize only to a specific marker, such a genetic signature-specific marker shown in the Tables below. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log } [Na+] + 0.41(\% \ G+C) - 0.63$$
$$(\% \text{ formamide}) - 600/\#bp \text{ in duplex}$$

As an illustration of the above formula, using [Na+]= [0.368] and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide" or "oligo" as used herein means a short sequence of DNA or DNA derivatives typically 8 to 35 nucleotides in length, primers, or probes. An oligonucleotide can be derived synthetically, by cloning or by amplification. An oligo is defined as a nucleic acid molecule comprised of two or more ribo- or deoxyribonucleotides, preferably more than three. The exact size of the oligonucleotide will depend on various factors and on the particular application and use of the oligonucleotide. The term "derivative" is intended to include any of the above described variants when comprising an additional chemical moiety not normally a part of these molecules. These chemical moieties can have varying purposes including, improving solubility, absorption, biological half life, decreasing toxicity and eliminating or decreasing undesirable side effects.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

A "siRNA" refers to a molecule involved in the RNA interference process for a sequence-specific post-transcriptional gene silencing or gene knockdown by providing small interfering RNAs (siRNAs) that has homology with the sequence of the targeted gene. Small interfering RNAs (siRNAs) can be synthesized in vitro or generated by ribonuclease III cleavage from longer dsRNA and are the mediators of sequence-specific mRNA degradation. Preferably, the siRNA of the invention are chemically synthesized using appropriately protected ribonucleoside phosphoramidites and a conventional DNA/RNA synthesizer. The siRNA can be synthesized as two separate, complementary RNA molecules, or as a single RNA molecule with two complementary regions. Commercial suppliers of synthetic RNA molecules or synthesis reagents include Applied Biosystems (Foster City, Calif., USA), Proligo (Hamburg, Germany), Dharmacon Research (Lafayette, Colo., USA), Pierce Chemical (part of Perbio Science, Rockford, Ill., USA), Glen Research (Sterling, Va., USA), ChemGenes (Ashland, Mass., USA) and Cruachem (Glasgow, UK). Specific siRNA constructs for inhibiting elevated mRNA levels associated with Ischemic Stroke may be between 15-35 nucleotides in length, and more typically about 21 nucleotides in length.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and Atransduction@ refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, peptide-tethering, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the Ischemic Stroke specific marker nucleic acid molecule(s) such that the latter is transcribed into mRNA. Host cell machinery then translates mRNA into a polypeptide.

Those skilled in the art will recognize that a nucleic acid vector can contain nucleic acid elements other than the promoter element and the Ischemic Stroke specific marker gene nucleic acid molecule(s). These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated genetic signature nucleic acid or biomarker molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long. One or both members of the pair may optionally comprise a detectable label.

"Sample" or "patient sample" or "biological sample" generally refers to a sample which may be tested for a particular molecule or combination of molecules, preferably a combination of the biomarker or genetic signature marker molecules, such as a combination of the markers shown in the Tables below. Samples may include but are not limited to peripheral blood, cells, and other body fluids, serum, plasma, CNS fluid, urine, saliva, tears, buccal swabs and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, small molecules, antibodies, peptides, peptide/DNA complexes, and any nucleic acid based molecule, for example an oligo, which exhibits the capacity to modulate the activity of the genetic signature nucleic acids described herein or their encoded proteins. Agents are evaluated for potential biological activity by inclusion in screening assays described herein below.

The term "modulate" as used herein refers increasing or decreasing. For example, the term modulate refers to the ability of a compound or test agent to either interfere with, or augment signaling or activity of a gene or protein of the present invention.

Methods of Using the Biomarkers and Genetic Signatures of the Invention

Genetic signature or biomarker encoding nucleic acids, including but not limited to those listed in Tables 4 and 5 herein below may be used for a variety of purposes in accordance with the present invention. The genetic signature associated with an increased risk of ischemic stroke (e.g., the plurality of nucleic acids contained therein) containing DNA, RNA, or fragments thereof may be used as probes to detect the presence of and/or expression of these specific markers in a biological sample. Methods in which such marker nucleic acids may be utilized as probes for such assays include, but are not limited to: (1) in situ hybridization; (2) Southern hybridization (3) northern hybridization; and (4) assorted amplification reactions such as high throughput reverse transcription, quantitative polymerase chain reactions (HT RT qPCR) or conventional PCR.

Further, assays for detecting the genetic signature may be conducted on any type of biological sample, but is most preferably performed on peripheral blood. From the foregoing discussion, it can be seen that genetic signature containing nucleic acids, vectors expressing the same, genetic signature encoded proteins and anti-genetic signature encoded protein specific antibodies of the invention can be used to detect the signature in body tissue, cells, or fluid, and alter genetic signature containing marker protein expression for purposes of assessing the genetic and protein interactions involved in ischemic stroke.

In certain embodiments for screening for genetic signature containing nucleic acid(s), the sample will initially be amplified, e.g. using high throughput RT-qPCR, to increase the amount of the template as compared to other sequences present in the sample. This allows the target sequences to be detected with a high degree of sensitivity if they are present in the sample. This initial step may be avoided by using highly sensitive array techniques that are becoming increasingly important in the art.

Alternatively, additional detection technologies can be employed which detect the ischemic stroke biomarker proteins directly. Such methods include geLC/MS/MS proteomics analysis. This approach provides a full panel of the protein biomarkers present in the sample and allows the clinician to predict outcomes based on the panel of biomarkers present in a sample.

Thus, any of the aforementioned techniques may be used to detect or quantify genetic signature expression and or protein expression levels and accordingly, diagnose patient susceptibility for developing ischemic stroke.

Kits and Articles of Manufacture

Any of the aforementioned products can be incorporated into a kit which may contain genetic signature polynucleotides or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, reagents and vessels suitable for obtaining a peripheral blood sample, reagents suitable for HT RT-qPCR, conventional PCR or any combination thereof.

Methods of Using the Genetic Signature or Biomarker Proteins for Development of Therapeutic Agents Since the genetic signature identified herein and the proteins encoded thereby have been associated with the etiology of ischemic stroke, methods for identifying agents that modulate the activity of the genes and their encoded products should result in the generation of efficacious therapeutic agents for the treatment of neurological and cardiovascular disorders, particularly those associated with ischemic stroke.

The nucleic acids comprising the signature contain regions which provide suitable targets for the rational design of therapeutic agents which modulate their activity. Small peptide molecules corresponding to these regions may be used to advantage in the design of therapeutic agents which effectively modulate the activity of the encoded proteins. Molecular modeling should facilitate the identification of specific organic molecules with capacity to bind to the active site of the proteins encoded by the genetic signature nucleic acids based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), Chem Div (San Diego, Calif.). The skilled person is aware of other sources and can readily purchase the same. Once therapeutically efficacious compounds are identified in the screening assays described herein, they can be formulated in to pharmaceutical compositions and utilized for the treatment of ischemic stroke patients.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the biomarker polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered ischemic stroke associated gene. These host cell lines or cells are defective at the polypeptide level. The host cell lines or cells are grown in the presence of drug compound. The effect on cell morphology and/or proliferation of the host cells is measured to determine if the compound is capable of regulating the same in the defective cells. Host cells contemplated for use in the present invention include but are not limited to bacterial cells, fungal cells, insect cells, mammalian cells, particularly neuronal, vascular, neutrophils, fibroblast, and CNS cells. The genetic signature encoding DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

Cells and cell lines suitable for studying the effects of genetic signature expression on cellular morphology and signaling methods of use thereof for drug discovery are provided. Such cells and cell lines will be transfected with one, two, three or all of the genetic signature encoding nucleic acids described herein and the effects on cell functions and cell signaling can be determined. Such cells and cell lines can also be contacted with the siRNA molecules provided herein to assess the effects thereof on similar functions. The siRNA molecules will be tested alone and in combination of 2, 3, 4, and 5 siRNAs to identify the most efficacious combination for down regulating target nucleic acids.

A wide variety of expression vectors are available that can be modified to express the novel DNA or RNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIP5, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, as well as neuronal-specific platelet-derived growth factor promoter (PDGF).

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the genetic signature of the present invention or functional fragments thereof provide a system in which to screen potential compounds or agents for the ability to modulate the development of acute ischemic stroke Another approach entails the use of phage display libraries engineered to express fragment of the polypeptides encoded by the genetic signature containing nucleic acids on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacophore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacophore.

Thus, one may design drugs which have, e.g., improved polypeptide activity or stability or which act as inhibitors, agonists, antagonists, etc. of polypeptide activity. By virtue of the availability of the genetic signature containing nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of genetic signature containing nucleic acids enables the production of strains of laboratory mice carrying the signature(s) of the invention. Transgenic mice expressing the genetic signature of the invention provide a model system in which to examine the role of the protein(s) encoded by the signature containing nucleic acid in the development and progression towards ischemic stroke. Methods of introducing transgenes in laboratory mice are known to those of skill in the art. Three common methods include: (1) integration of retroviral vectors encoding the foreign gene of interest into an early embryo; (2) injection of DNA into the pronucleus of a newly fertilized egg; and (3) the incorporation of genetically manipulated embryonic stem cells into an early embryo. Production of the transgenic mice described above will facilitate the molecular elucidation of the role that a target protein plays in various cellular metabolic processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extra-chromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of genetic signature containing nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use genetic signature associated genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extra-chromosomal recombination, which occurs at a frequency approaching 100%, homologous plasmid-chromosome recombination was originally reported to only be detected at frequencies between $10^{-6}$ and $10^{-3}$. Non-homologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabino-fluranosyl)-5-iodou-racil, (FIAU). By this counter selection, the number of homologous recombinants in the surviving transformants can be increased. Utilizing genetic signature containing nucleic acid as a targeted insertional cassette provides means to detect a successful insertion as visualized, for example, by acquisition of immunoreactivity to an antibody immunologically specific for the polypeptide encoded genetic signature nucleic acid(s) and, therefore, facilitates screening/selection of ES cells with the desired genotype.

As used herein, a knock-in animal is one in which the endogenous murine gene, for example, has been replaced with human genetic signature-associated gene(s) of the invention. Such knock-in animals provide an ideal model system for studying the development of acute ischemic stroke.

As used herein, the expression of a genetic signature containing nucleic acid, fragment thereof, or genetic signature fusion protein can be targeted in a "tissue specific manner" or "cell type specific manner" using a vector in which nucleic acid sequences encoding all or a portion of genetic signature-associated protein are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific expression of proteins are well known in the art and described herein.

Methods of use for the transgenic mice of the invention are also provided herein. Transgenic mice into which a nucleic acid containing the genetic signature or its encoded protein(s) have been introduced are useful, for example, for use in screening methods to identify therapeutic agents modulate or ameliorate the symptoms of ischemic stroke.

Pharmaceuticals and Peptide Therapies

The elucidation of the role played by the gene products described herein in ischemic stroke occurrence facilitates the development of pharmaceutical compositions useful for the diagnosis, management and treatment of ischemic stroke. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

As it is presently understood, RNA interference involves a multi-step process. Double stranded RNAs are cleaved by the endonuclease Dicer to generate nucleotide fragments (siRNA). The siRNA duplex is resolved into 2 single stranded RNAs, one strand being incorporated into a protein-containing complex where it functions as guide RNA to direct cleavage of the target RNA (Schwarz et al, Mol. Cell. 10:537 548 (2002), Zamore et al, Cell 101:25 33 (2000)), thus silencing a specific genetic message (see also Zeng et al, Proc. Natl. Acad. Sci. 100:9779 (2003)).

Pharmaceutical compositions that are useful in the methods of the invention may be administered systemically in parenteral, oral solid and liquid formulations, ophthalmic, suppository, aerosol, topical or other similar formulations. These pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate agent to a patient according to the methods of the invention. The use of nanoparticles to deliver agents, as well as cell membrane permeable peptide carriers that can be used are described in Crombez et al., Biochemical Society Transactions v35:p 44 (2007).

In order to treat an individual having an acute ischemic stroke, to alleviate a sign or symptom of the disease, the pharmaceutical agents of the invention should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having, or at risk for an acute ischemic stroke.

In an individual suffering from an ischemic stroke, administration of the agent can be particularly useful when administered in combination, for example, with a conventional agent for treating ischemic stroke. The skilled artisan would administer the agent alone or in combination and would monitor the effectiveness of such treatment using routine methods such as sonogram, radiologic, immunologic or, where indicated, histopathologic methods. Other conventional agents for the treatment of ischemic stroke include agents, such as TPA and other anticoagulants. Administration of the pharmaceutical preparation is preferably in an "effective amount" this being sufficient to show benefit to the individual. This amount prevents, alleviates, abates, or otherwise reduces the severity of ischemic stroke symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art.

The following methods are provided in detail to facilitate the practice of the present invention.

Study Subjects

Peripheral blood samples were obtained from 18 ischemic stroke patients admitted to the University Hospital of Brooklyn at SUNY Downstate Medical Center and at Long Island College Hospital and 15 gender and race matched control subjects recruited from the local community. The median time of blood draw was 36 hours post stroke onset. Stroke was diagnosed according to World Health Organization stroke criteria. The Institutional Review Board at the State University of New York (SUNY) approved the study and all study participants or their authorized representatives gave full and signed informed consent.

The study inclusion criteria were: over 18 years of age and acute ischemic stroke. The exclusion criteria were: current immunological diseases, taking steroid or immunosuppressive therapies, severe allergies, acute infection and severe anemia. The following clinical data were recorded: age, gender, race, self-reported risk factors, National Institutes of Health Stroke Scale (NIHSS) score in the stroke subjects and complete blood counts (CBC), including total white blood cell count and white cell differential counts. Hypertension was defined as a prior (at any time in the past) diagnosis of hypertension by the subject's physician or currently receiving treatment for hypertension. Diabetes was defined as a past medical history of known diabetes mellitus. Coronary artery disease was defined as a physician-diagnosed past history of ischemic heart disease or angina. Hyperlipidemia was defined as a past history of documented elevation in total cholesterol (>200 mg/dl). Smoking was defined as current or prior smoking Atrial fibrillation was defined as a past or current history of physician-diagnosed atrial fibrillation.

TABLE 1

Clinical and laboratory characteristics of patients and controls

| Factor | All (n = 33) | Stroke (n = 18) | Control (n = 15) | p |
|---|---|---|---|---|
| Age | 65.4 ± 14.3 | 71.6 ± 13.0 | 58.1 ± 12.3 | 0.004 |
| Gender - male | 14 (42) | 7 (39) | 7 (47) | 0.9 |
| Race - black | 30 (91) | 17 (94) | 13 (87) | 0.9 |
| Risk factors | | | | |
| Hypertension | 28 (85) | 17 (94) | 11 (73) | 0.2 |
| Diabetes | 15 (45) | 8 (39) | 7 (53) | 0.6 |
| Coronary artery disease | 8 (24) | 5 (28) | 3 (20) | 0.9 |
| Smoking history | 7 (21) | 5 (28) | 2 (13) | 0.6 |
| Atrial fibrillation | 4 (12) | 4 (22) | 0 (0) | 0.2 |
| Hyperlipidemia | 16 (48) | 8 (44) | 8 (53) | 0.9 |
| Medications | | | | |
| Diuretics | 9 (27) | 6 (33) | 3 (15) | 0.6 |
| ACEIs/ARBs | 9 (27) | 7 (39) | 2 (13) | 0.2 |
| Beta blockers | 21 (64) | 14 (78) | 7 (47) | 0.1 |
| Calcium channel blockers | 8 (24) | 5 (28) | 3 (20) | 0.9 |
| Anti-thrombotics | 18 (54) | 10 (55) | 8 (53) | 1.0 |
| Statins | 14 (42) | 7 (39) | 7 (47) | 0.9 |
| WBC count ($10^9$ cells/liter) | 6.9 ± 2.4 | 7.45 ± 2.2 | 6.18 ± 2.6 | 0.2 |
| Stroke-Related | | | | |
| Time of blood draw (hours) | N/A | 36.0 (23.0, 48.0) | N/A | N/A |
| Infarct volume ($mm^3$) | N/A | 5404.0 (1,207.0, 22,870.0)) | N/A | N/A |
| NIHSS score | N/A | 7.5 (4.2, 10.0) | N/A | N/A |

Primer Selection and Development 40 transcripts identified in 3 previously published studies [4-6] were selected for analysis (Table 2). The 3 studies had identified 9, 18 and 22 genes within panels with some overlap among the studies. Hox 1.11, transcript identified in Tang's et al. study[5], was not studied because it is a non-coding RNA sequence. Hypothetical protein FLJ22662 Laminin A motif from the Moore list[4] is now termed phospholipase B domain containing 1 (PLBD1) according to current nomenclature. Two variants of CD14 were studied to give a total of 41 transcripts that were tested. The complete primer characteristics were published earlier[18]. The RT-qPCR primers were self-designed, commercially synthesized by Invitrogen and wet tested using regular RT-qPCR (StepOnePlus Real-Time PCR Systems; Applied Biosystems).

TABLE 2

Comparison of 41 transcripts between stroke and control subjects

| Transcript | Cellular source (reference) | Fold change | p value | Adjusted p value* | Adjusted p value** |
|---|---|---|---|---|---|
| CD163 | PBMC[4] | 2.22 | 0.069 | 0.14 | 1.0 |
| PLBD1 | PBMC[4] | 3.18 | 0.0034 | 0.03 | 0.14 |
| ADM | PBMC[4] | 1.85 | 0.0066 | 0.03 | 0.27 |
| KIAA0146 | PBMC[4] | 1.21 | 0.43 | 0.52 | 1.0 |
| APLP2 | PBMC[4] | 1.08 | 0.56 | 0.62 | 1.0 |
| NPL | PBMC[4], WB[5] | 1.67 | 0.094 | 0.16 | 1.0 |
| FOS | PBMC[4] | 2.64 | 0.043 | 0.10 | 1.0 |
| TLR2 | PBMC[4] | 1.37 | 0.57 | 0.62 | 1.0 |
| NAIP | PBMC[4] | 1.71 | 0.24 | 0.34 | 1.0 |
| CD36 | PBMC[4] | 2.11 | 0.29 | 0.10 | 1.0 |
| DUSP1 | PBMC[4] | 2.89 | 0.033 | 0.10 | 1.0 |
| ENTPD1 | PBMC[4] | 2.03 | 0.039 | 0.10 | 1.0 |
| VCAN | PBMC[4], WB[6] | 2.36 | 0.058 | 0.13 | 1.0 |
| CYBB | PBMC[4] | 2.61 | 0.0083 | 0.04 | 0.34 |
| IL13RA1 | PBMC[4] | 1.58 | 0.10 | 0.16 | 1.0 |
| LTA4H | PBMC[4] | 1.61 | 0.20 | 0.30 | 1.0 |
| ETS2 | PBMC[4], WB[5] | 2.86 | 0.017 | 0.07 | 0.70 |
| CD14-1 | PBMC[4] | 1.93 | 0.065 | 0.14 | 1.0 |
| CD14-2 | PBMC[4] | 1.39 | 0.74 | 0.78 | 1.0 |
| BST1 | PBMC[4] | 6.42 | 0.0035 | 0.03 | 0.14 |
| CD93 | PBMC[4] | 2.11 | 0.00086 | 0.02 | 0.03 |
| PILRA | PBMC[4] | 1.29 | 0.56 | 0.62 | 1.0 |
| FCGR1A | PBMC[4] | 3.28 | 0.076 | 0.14 | 1.0 |
| CKAP4 | WB[5] | 1.93 | 0.0040 | 0.03 | 0.14 |
| S100A9 | WB[5] | 3.84 | 0.0014 | 0.02 | 0.06 |
| MMP9 | WB[5,6] | 2.21 | 0.10 | 0.16 | 1.0 |
| S100P | WB[5] | 2.67 | 0.0399 | 0.10 | 1.0 |
| F5-1 | WB[5] | 2.14 | 0.034 | 0.10 | 1.0 |
| FPR1 | WB[5] | 1.79 | 0.07 | 0.14 | 1.0 |
| S100A12 | WB[5,6] | 2.93 | 0.000593 | 0.02 | 0.02 |
| RNASE2 | WB[5] | 1.06 | 0.84 | 0.86 | 1.0 |
| ARG1 | WB[5,6] | 1.34 | 0.34 | 0.42 | 1.0 |
| CA4 | WB[5,6] | 1.74 | 0.17 | 0.27 | 1.0 |
| LY96 | WB[5,6] | 1.41 | 0.27 | 0.36 | 1.0 |
| SLC16A6 | WB[5] | 1.64 | 0.23 | 0.34 | 1.0 |
| HIST2H2AA3 | WB[5] | 1.48 | 0.25 | 0.34 | 1.0 |
| BCL6 | WB[5] | 0.97 | 0.58 | 0.62 | 1.0 |
| PYGL | WB[5] | 2.55 | 0.0059 | 0.03 | 0.24 |
| CCR7 | WB[6] | 0.995 | 0.96 | 0.96 | 1.0 |
| IQGAP1 | WB[6] | 1.67 | 0.04 | 0.10 | 1.0 |
| ORM1 | WB[6] | 1.28 | 0.31 | 0.40 | 1.0 |

*FDR method,
**Bonferroni method
Wilcoxon rank sum tests and t tests used for analyses

TABLE 3

Primers used for amplification of markers

| Name | Name | RefSeq | gene ID NCBI | Variants | Forward primer | Reverse primer |
|---|---|---|---|---|---|---|
| F5 | F5; coagulation factor V (proaccelerin, labile factor) | NM_000130.4 | 2153 | | AAATCCCATGAG TTTCACGCC (SEQ ID NO: 1) | CAGACCCCTAA CTGGTGCTGTT (SEQ ID NO: 41) |
| S100A9 | S100A9; S100 calcium binding protein A9 | NM_002965.3 | 6280 | | CTCGGCTTTGAC AGAGTGCAAGA C (SEQ ID NO: 2) | TCCCCGAGGCC TGGCTTATGG (SEQ ID NO: 42) |
| CD163 | CD163 molecule | NM_004244.4 | 9332 | two variants (2 variants) | GCCACAACAGGT CGCTCATCCC (SEQ ID NO: 3) | GGCTCAGAATG GCCTCCTTTTCC A (SEQ ID NO: 43) |
| TLR2 | toll-like receptor 2 | NM_003264.3 | 7097 | | GCTGCTCGGCGT TCTCTCAGG (SEQ ID NO: 4) | TGTCCAGTGCTT CAACCCACAAC T (SEQ ID NO: 44) |
| ENTPD1 | ectonucleoside triphosphate diphospho-hydrolase 1 (ENTPD1) | NM_001098175.1 | 953 | seven variants (for 1,2,3,4,5: 254n) | GCATGCGGTTGC TCAGGATGGAA A (SEQ ID NO: 5) | GGCTCCCCCAA GGTCCAAAGC (SEQ ID NO: 45) |
| VCAN | versican (VCAN), | NM_001126336.2 | 1462 | four variants (2nd variant) | AAACGACCTGAT CGCTGCAAAATG A (SEQ ID NO: 6) | GGCCGCAAGCG ACTGTTCCTT (SEQ ID NO: 46) |
| CD14 | CD14 molecule (CD14), | NM_001040021.2 | 929 | four variants (2nd variant) | CCCCTTGGTGCC AACAGATGAGG (SEQ ID NO: 7) | CGGCTGCCTCTT ATATCCCAGAG A (SEQ ID NO: 47) |
| CD14 | CD14 molecule (CD14), | NM_001174104.1 | 929 | four variants (3rd variant) | GGTGCCAACAG ATGAGGTTCACA (SEQ ID NO: 8) | AGCCAGCCCCC TTCCTTTCCTTA (SEQ ID NO: 48) |
| ADM | adrenomedullin (ADM), | NM_001124.1 | 133 | | CTTAGCAGGGTC TGCGCTTCGC (SEQ ID NO: 9) | CGAGCGGTGTC AGCGCCTAG (SEQ ID NO: 49) |
| DUSP1 | phosphatase 1 (DUSP1 | NM_004417.3 | 1843 | | TACGATCAGGGT GGCCCGGTG (SEQ ID NO: 10) | AGGTGCCTCGG TCGAGCACA (SEQ ID NO: 50) |
| CYBB | cytochrome b-245, beta polypeptide (CYBB), | NM_000397.3 | 1536 | | TCCAGTGCGTGC TGCTCAACAA (SEQ ID NO: 11) | TCTGCGGTCTGC CCACGTAC (SEQ ID NO: 51) |
| LTA4H | leukotriene A4 hydrolase (LTA4H) | NM_000895.1 | 4048 | | GGGCACCTCTTC CATTGGGGC (SEQ ID NO: 12) | GCAGAGCCGCA GCCATCTGAA (SEQ ID NO: 52) |
| CD36 | CD36 molecule (thrombo-spondin receptor) (CD36 | NM_001001548.2 | 948 | five variants (1st variant) | TCAGCAAATGCA AAGAAGGGAGA CC (SEQ ID NO: 13) | GAGGATGACAG GAATGCAGGGC C (SEQ ID NO: 53) |

TABLE 3-continued

Primers used for amplification of markers

| Name | Name | RefSeq | gene ID NCBI | Variants | Forward primer | Reverse primer |
|---|---|---|---|---|---|---|
| NAIP | NLR family, apoptosis inhibitory protein (NAIP) | v1: NM_004536.2; v2: NM_022892.1; and two other products | 4671 | two variants (two variants) and two extra products | ACTGGCCCCGGG AATCAGCT (SEQ ID NO: 14) | TCACCCTGTGCC ATTTCTGGCA (SEQ ID NO: 54) |
| APLP2 | amyloid beta (A4) precursor-like protein 2 (APLP2) | v1: NM_001642.2; v2: NM_001142276.1; v3: NM_001142277.1; | 334 | four variants (for 1st, 2nd and 3rd variant) | GGCCGGCTACAT CGAGGCTCT (SEQ ID NO: 15) | CCGTGTGCCAG TGCTGGTGA (SEQ ID NO: 55) |
| FOS | Homo sapiens FBJ murine osteosarcoma viral oncogene homolog (FOS) | NM_005252.3 | 2353 | | CCCCTCCGCTGG GGCTTACT (SEQ ID NO: 16) | GGTCTGTCTCCG CTTGGAGTGT (SEQ ID NO: 56) |
| IL13RA1 | IL13RA1 interleukin 13 receptor, alpha 1 | NM_001560.2 | 3597 | | GCGCCTACGGAA ACTCAGCCACC (SEQ ID NO: 17) | TGGTGCTACAC TGGGACCCAC (SEQ ID NO: 57) |
| BST1 | BST1 bone marrow stromal cell antigen 1 | NM_004334.2 | 683 | | TGAGTCCCGAGC AGCGGAACAA (SEQ ID NO: 18) | GCTGCCTTCCCC GCAGGATT (SEQ ID NO: 58) |
| CD93 | CD93 CD93 molecule | NM_012072.3 | 22918 | | TGGCAGGCTGGG TCCCTCTC (SEQ ID NO: 19) | TCCCCATGGCC CTGGCTTGT (SEQ ID NO: 59) |
| PILRA | PILRA paired immunoglobin-like type 2 receptor alpha | NM_178272.1 | 29992 | three variants (2nd variant) | AAACTCTCCATC ACCCAGGGTCAG (SEQ ID NO: 20) | AGCTGGAGAGG GCAAGGGAAGC (SEQ ID NO: 60) |
| FCGR1A | FCGR1A Fc fragment of IgG, high affinity Ia, receptor (CD64) | NM_000566.3 | 2209 | | GCAAGTGGACA CCACAAAGGCA G (SEQ ID NO: 21) | ACCAGGCCTCT GCAAGAGCAAC (SEQ ID NO: 61) |
| ETS2 | ETS2 v-ets erythro-blastosis virus E26 oncogene homolog 2 (avian) | NM_005239.4 | 2114 | | CTGGCCGGCTTC ACAGGAAGT (SEQ ID NO: 22) | TGGTCCCGGCG ACCTCAGTC (SEQ ID NO: 62) |
| KIAA0146 | KIAA0146 KIAA0146 | NM_001080394.1 | 23514 | | CCGCGCTCGGGG CTCTAAGAG (SEQ ID NO: 23) | GGTGGTTTCTTG CTTGGGTCTAG GG (SEQ ID NO: 63) |
| PLBD1 | PLBD1 phospholipase B domain containing 1 | NM_024829.5 | 79887 | | GGGTTACCTCAC TGCCCCACACAT (SEQ ID NO: 24) | GCGGAGCAATG TCCCATGTCCC (SEQ ID NO: 64) |
| CKAP4 | cytoskeleton-associated protein 4 | NM_006825.3 | 10970 | | CGAGCAGAAGG TGCAGTCTTTGC AA (SEQ ID NO: 25) | AGCCGCTCCTC CACCGTGTT (SEQ ID NO: 65) |

TABLE 3-continued

Primers used for amplification of markers

| Name | Name | RefSeq | gene ID NCBI | Variants | Forward primer | Reverse primer |
|---|---|---|---|---|---|---|
| MMP9 | matrix metallo-peptidase 9 (gelatinase B, 92kDa gelatinase, 92kDa type IV collagenase) | NM_004994.2 | 4318 | | GGGCCGCTCCTA CTCTGCCT (SEQ ID NO: 26) | ACCGTCGAGTC AGCTCGGGT (SEQ ID NO: 66) |
| S100P | S100 calcium binding protein P | NM_005980.2 | 6286 | | CGATATTCGGGC AGCGAGGGC (SEQ ID NO: 27) | CTTTTCCACTCT GCAGGAAGCCT G (SEQ ID NO: 67) |
| FPR1 | formyl peptide receptor 1 | v1: NM_001193306.1; v2: NM_002029.3 | 2357 | two variants (for two variants) | CCTGAACCTGGC CGTGGCTG (SEQ ID NO: 28) | CGGTGCGGTGG TTCTGGGTC (SEQ ID NO: 68) |
| S100A12 | S100 calcium binding protein A12 | NM_005621.1 | 6283 | | TTGAGGGGTTAA CATTAGGCTGGG A (SEQ ID NO: 29) | GCAGCCTTCAG CGCAATGGC (SEQ ID NO: 69) |
| RNASE2 | ribonuclease, RNase A family, 2 (liver, eosinophil-derived neurotoxin) | NM_002934.2 | 6036 | | GCCCCTGAACCC CAGAACAACCA (SEQ ID NO: 30) | ACCATGTTTCCC AGTCTCCGCGC (SEQ ID NO: 70) |
| ARG1 | arginase, liver | NM_000045.2 | 383 | | GGCGGAGACCA CAGTTTGGCAAT (SEQ ID NO: 31) | GACCTCCCACG ACTGGTGTGC (SEQ ID NO: 71) |
| CA4 | carbonic anhydrase IV | NM_000717.3 | 762 | | TCGGCCAGTGCA GAGTCACAC (SEQ ID NO: 32) | GGGGGACTGGC GGTCCTTCT (SEQ ID NO: 72) |
| LY96 | lymphocyte antigen 96 | v1: NM_015364.4; v2: NM_001195797.1; | 23643 | two variants (for all) | GAGCTCTGAAGG GAGAGACTGTG A (SEQ ID NO: 33) | AAGAGCATTTC TTCTGGGCTCCC A (SEQ ID NO: 73) |
| SLC16A6 | solute carrier family 16, member 6 | v1: NM_001174166.1; v2: NM_004694.4; | 9120 | two variants (for all) | GGACCGCCCCTT GCAGGTTT (SEQ ID NO: 34) | CACCAGGGCGA GGCACACAG (SEQ ID NO: 74) |
| HIST2H 2AA3 and HIST2H 2AA4 | histone cluster 2, H2aa3 and histone cluster 2, H2aa4 | AA3 gene: NM_003516.2; AA4 gene NM_001040874.1; | AA3: 8337; AA4: 723790 | two genes (for two) | TTCCCGATCGCC AGGCAGGA (SEQ ID NO: 35) | TTGCCTTTGCGC AGCAAGCG (SEQ ID NO: 75) |
| BCL6 | B-cell CLL/lymphom a 6 | NM_001134738.1 | 604 | three variants (3rd variant) | GAAGTGCACGTC CTGCGGCT (SEQ ID NO: 36) | GCAACGATAGG GTTTCTCACCAC A (SEQ ID NO: 76) |
| PYGL | phosphorylase, glycogen, liver | NM_001163940.1 | 5836 | two variants (2nd variant) | CTACGACAAGTG CCCCAAGCTT (SEQ ID NO: 37) | GCTGGATGGCC ACCTGATCCG (SEQ ID NO: 77) |

TABLE 3-continued

Primers used for amplification of markers

| Name | Name | RefSeq | gene ID NCBI | Variants | Forward primer | Reverse primer |
|---|---|---|---|---|---|---|
| CCR7 | chemokine (C-C motif) receptor 7 | NM_001838.3 | 1236 | | TCCCCAGACAGG GGTAGTGCG (SEQ ID NO: 38) | CATTGGTTTCCC CAGGTCCATGA CG (SEQ ID NO: 78) |
| IQGAP1 | IQ motif containing GTPase activating protein 1 | NM_003870.3 | 8826 | | CGCGCCTCCAAG GTTTCACG (SEQ ID NO: 39) | TCCAGGACAGA GCCATAGTGCG G (SEQ ID NO: 79) |
| ORM1 | orosomucoid 1 | NM_000607.2 | 5004 | | CCAGATACGTGG GAGGCCAAGAG (SEQ ID NO: 40) | GCCCCCAGTTCT TCTCATCGTTCA (SEQ ID NO: 80) |

Sample Processing

Where applicable the conduct and reporting of the study are in accordance with the Minimum Information for Publication of Quantitative Real-Time PCR Experiments criteria [19]. RNA was extracted using column separation (All-in-One Kit; Norgen Biotek, Thorold, Ontario, Canada) from 100 µl of whole blood collected on ethylenediaminetetraacetic acid tubes (ETDA). Cell count (millions of cells per µl) was based on white blood cell (WBC) count from laboratory CBC obtained for each study subject. cDNA was synthetized using the High Capacity cDNA Reverse Transcription Kit (Life Technologies, Carlsbad, Calif.), based on random hexamers, according to the manufacturer's protocol. In addition to study samples two commercial cDNA samples (Universal cDNA Reverse Transcribed by Random Hexamer: Human Normal Tissues; Biochain, Newark, Calif.) were run on each plate to perform normalization. HT RT-qPCR was run on the BioMark HD System, using 96×96 Fluidigm Dynamic Arrays (Fluidigm, South San Francisco, Calif.). Three plates were used for this study. The percent present calls were over 90%.

Gene Expression Data Analyses and Development of the Gene Classifier

Gene expression for each sample was measured using the input sample quantity method [20] after adjusting for the input cell count and normalizing to a standard volume of a standard cDNA sample (Universal cDNA Reverse Transcribed by Random Hexamer: Human Normal Tissues; Biochain, Newark, Calif.). The normalized copy number for each sample was obtained according to the equation:

$$X_C = \frac{(1+E)^{(nCq, cDNA - nCq, X)}}{cc}$$

where $X_c$ is the transcript number per cell, E is the efficiency of target cDNA amplification, nCq, cDNA and nCq, X are the cycle number at which amplification crosses the threshold respectively for standard cDNA sample and for sample X, cc is the number of cells used for RNA extraction based on CBC result. The results for the stroke patients and control subjects were then compared. We have identified several predictive clusters, including a 7 gene classifier was identified from a hierarchical cluster analysis. The upper level of normal for the expression of each transcript was defined as a value above the third quartile in the control subjects. We have previously presented graphical results, based only on Cq values normalized to cell count, of four stroke related transcripts in a cohort of hemorrhagic and ischemic stroke patients.

Statistical Analyses

The data were analyzed using R version 2.15.1. Shapiro's tests were used to assess for normality of the data. For grouped and categorical data t tests, Mann Whiney U, Wilcoxon rank sum and Student's t tests were used to compare groups. Chi-square tests were used to compare categorical values. Spearman correlation coefficients were used to test the association of transcript expression with age and time of blood draw. Corrections for multiple comparisons used the Benjamini and Hochberg (false discovery rate, [FDR]) and Bonferroni algorithms. The hierarchical cluster analysis—a non-supervised technique to detect hidden associations in the data—used Ward's method and log-transformed data. The Ward algorithm employs an Euclidian distance measure. A cutoff ("height") level at "9" was used to give the 7 Clusters. Receiver operating curve analysis and sensitivity and specificity analyses were used to test diagnostic value of the 7 transcript cluster. p-values<0.05 were considered statistically significant.

The following examples are provided to illustrate certain embodiments of the invention. They are not intended to limit the invention in any way.

Example 1

Biomarkers Associated with Acute Ischemic Stroke and Next Generation QPCR and Validation Thereof We studied forty candidate markers identified in three gene expression profiles to (1) quantitate individual transcript expression, (2) identify transcript clusters and (3) assess the clinical diagnostic utility of the clusters identified for ischemic stroke detection. Using high throughput next generation qPCR 16 of the 40 transcripts were significantly up-regulated in stroke patients relative to control subjects (p<0.05). Several clusters of between 3 and 8 transcripts discriminated between stroke and control (p values between $1.01 \times 10^{-9}$ and 0.03; Table 4). A 7 transcript cluster containing PLBD1, PYGL, BST1, DUSP1, FOS, VCAN and FCGR1A showed high accuracy for stroke classification (AUC=0.854). A second 7 transcript cluster also proved effective at discriminating between stroke and control patients. This cluster included PILRA, BCL6, FPR1, LYS96, S100A9, S100A12 and MMP9. Moreover, using a panel including the 16 upregulated genes of FIG. 1 achieved p values of $10^{-12}$. The invention also entails analysis of all of the genes listed in Table 4. The invention described herein provides a plurality of validated and improved biomarker panels for diagnosis of acute ischemic stroke, streamlining the diagnostic process and reducing time between presentation and therapeutic intervention at the clinic.

Results

The patients and controls were matched on gender, race and stroke risk factors (Table 1). The mean age of the stroke patients was 71 years and of the controls was 58 years (p=0.004).

Whole Blood Expression of Stroke-Related Transcripts.

16 genes were significantly up-regulated in the stroke patients relative to the control subjects (p<0.05, Wilcoxon rank sum test, Table 2). The fold change differences for the 16 transcripts ranged from 6.4 for BST1 to 1.7 for IQGAP1 (FIG. 1). Nine genes were altered at the p<0.01 level: these were CD93, S100A9, CYBB, S100A12, BST1, PLBD1, PYGL, ADM and CKAP4. All of these 9 genes remained significant after corrections for multiple comparisons using the FDR method and two (S100A12 and CD93) using the Bonferroni method.

41% (9/22) of genes from the PBMC list were significantly altered. 38% (8/21) from the whole blood gene lists were significantly altered, 7 genes were on Tang et al. list and 2 were on Barr et al. list. One transcript was common to both the whole blood and PBMC lists (this was ETS2) and one transcript was common to both WB lists (S100A12). Although, modest correlations with age for two transcripts were identified—FOS (rho=0.42, p=0.02) and PYGL (rho=0.43, p=0.02), after corrections for multiple comparisons these correlations were no longer significant. There was no correlation of transcript copy number with gender or with the time of blood draw.

Clusters of Genes in Whole Blood

Figure 2A:
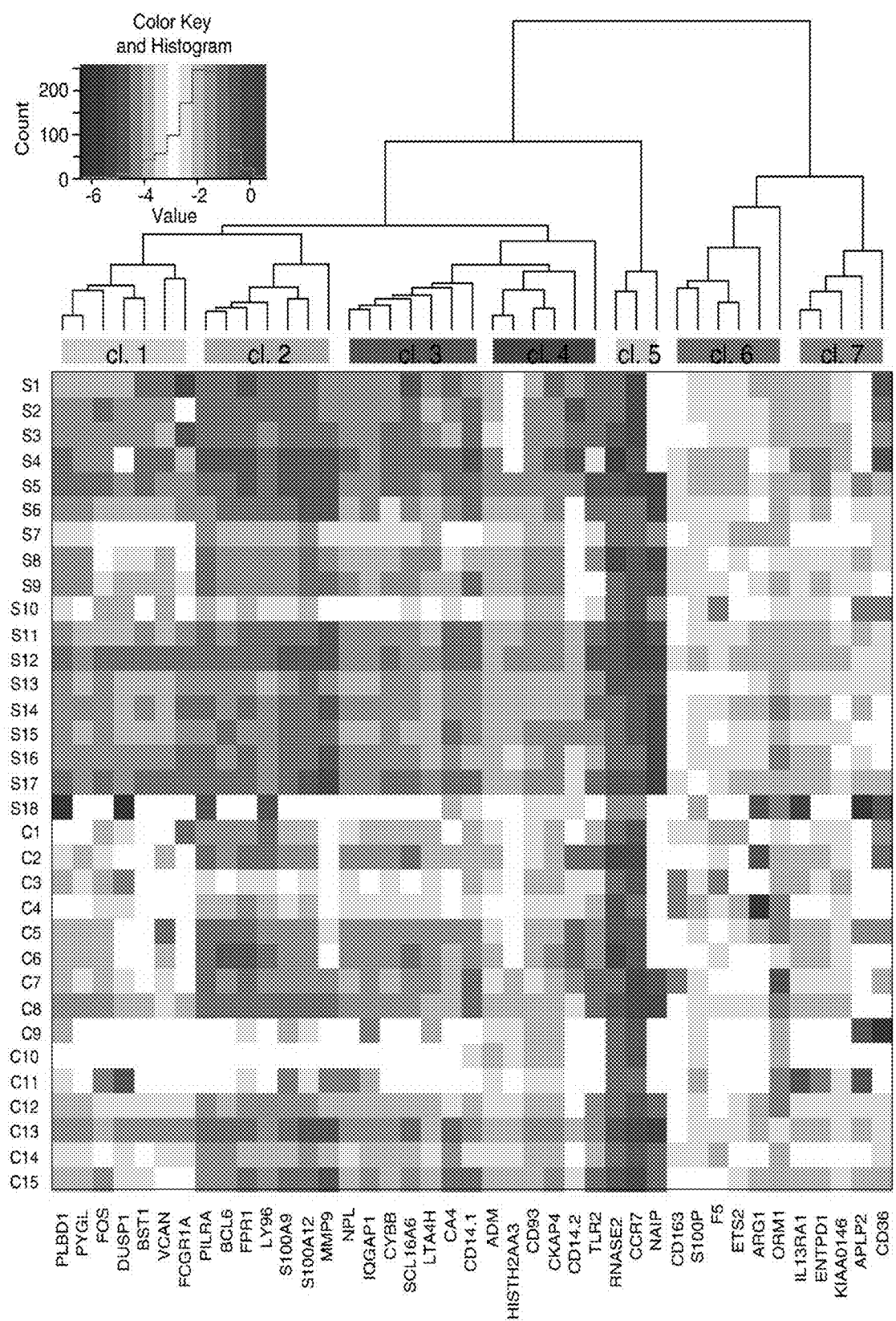
FIG. 2A Heatmap and Hierarchical Cluster Analysis This heatmap and hierarchical cluster analysis illustrates gene expression levels for the 41 studied genes in the control subjects (C) and stroke patients (S). Seven clusters (cl.1 to cl.7) are highlighted by seven squares of different color. Data are log-transformed. This demonstrates elevated expression of many transcripts in stroke patients relative to controls.
Figure 2B:
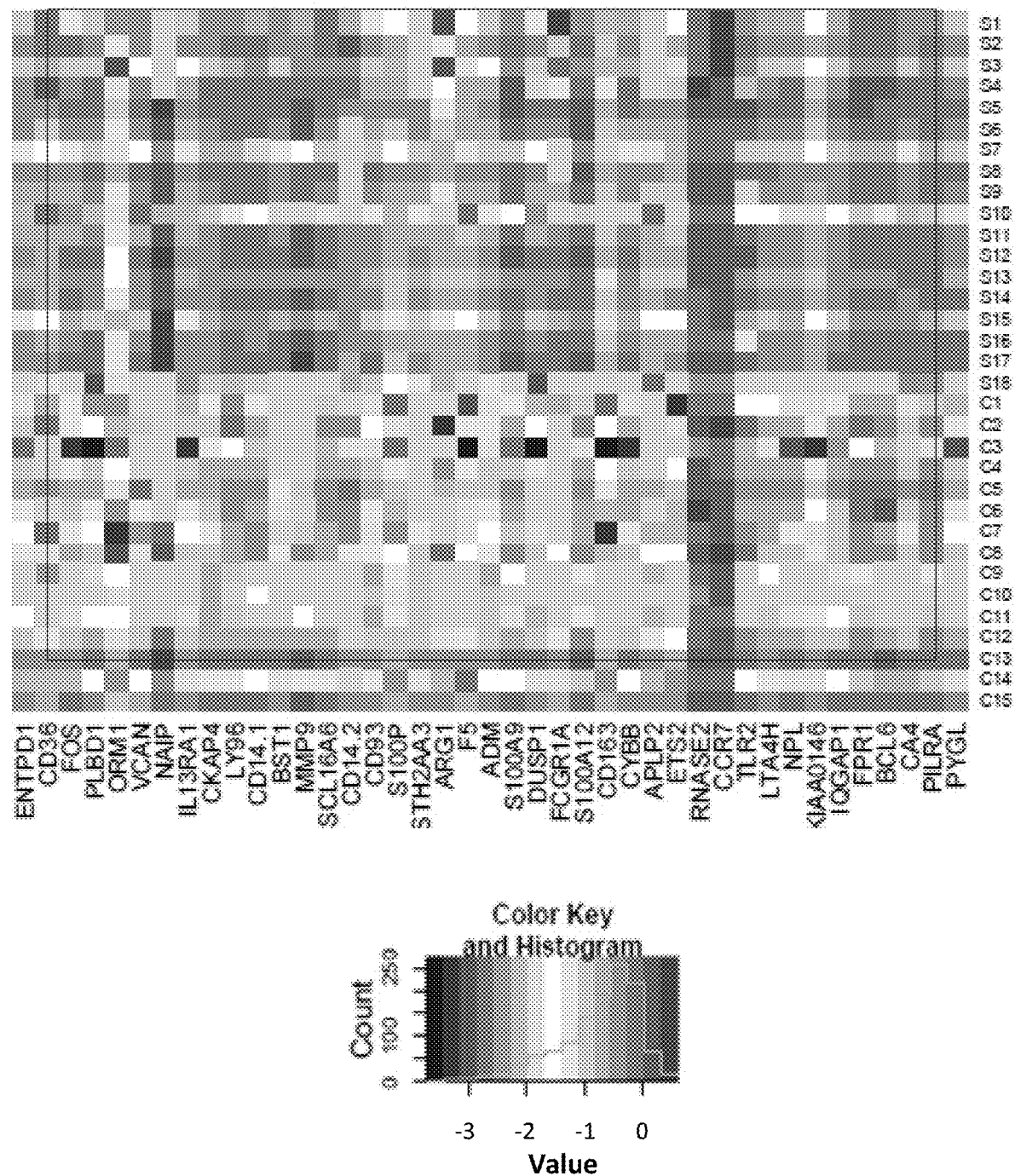
FIG. 2B is a heat map showing that the majority of the biomarkers identified where upregulated in stroke patients when compared to control subjects.

Several clusters of between 3 and 7 transcripts were identified in a hierarchical cluster analysis. (FIG. 2A). Six of these showed significant discrimination between stroke and control with p values for the six clusters ranging between $1.10\times1.^{-9}$ for Cluster 1 and 0.037 for Cluster 7 (Table 4). After correction for multiple comparisons using the Bonferroni method all but one remained significant. The clusters consisted of transcripts from both whole blood and PBMC studies. Based on the demonstration of the most significant discrimination between stroke and control Cluster 1 was selected for further study.

TABLE 4

Transcript clusters identified in hierarchical cluster analysis

| Transcripts | Cellular sources (number of genes) | P value, of cluster, stroke versus control | Adjusted p value* | Adjusted p value** |
|---|---|---|---|---|
| Cluster 1 7 genes PLBD1, PYGL, FOS, DUSP1, BST1, VCAN, FCGR1A | PBMC panel (5), both PBMC and WB panels (1), WB panel (1) | 1.01e−9 | 7.04e−9 | 7.04e−9 |
| Cluster 2 7 genes PILRA, BCL6, FPR1, LY96, S100A9, S100A12, MMP9 | WB panels (6), PBMC panel (1) | 1.50e−6 | 5.26e−6 | 1.05e−5 |
| Cluster 3 7 genes NPL, IQGAP1, CYBB, SLC16A6, LTA4H, CA4, CD14-1 | PBMC panel (3), PBMC and WB panels (1), WB panels (3) | 1.52e−5 | 3.55e−5 | 1.06e−4 |
| Cluster 4 6 genes ADM, HIST2H2AA3, CD93, CKAP4, CD14-2, TLR2 | PBMC panel (4), WB panel (2) | 0.0016 | 0.0022 | 0.011 |
| Cluster 5 3 genes NAIP, RNASE2, CCR7 | WB panels (2), PBMC panel (1) | 0.40 | 0.40 | 1.0 |
| Cluster 6 6 genes CD163, S100P, F5, ETS2, ARG1, ORM1 | WB panels (4), PBMC panel (1), WB and PBMC panels (1) | 0.00025 | 4.0e−4 | 1.61e−3 |
| Cluster 7 5 genes APLP2, IL13RA1, ENTPD1, KIAA0146, CD36 | PBMC panel (5) | 0.037 | 0.042 | 0.26 |
| Cluster 8 8 genes PLBD1, PYGL, BST1, DUSP1, FOS, | PBMC Panel and WB Panel | 4.7 × $10^{-11}$ | | |

TABLE 4-continued

Transcript clusters identified in hierarchical cluster analysis

| Transcripts | Cellular sources (number of genes) | P value, of cluster, stroke versus control | Adjusted p value* | Adjusted p value** |
|---|---|---|---|---|
| NPL, KIAA0146, ENTPD1 | | | | |
| Cluster 9 | PBMC Panel | $8.2 \times 10^{-8}$ | | |
| 6 genes | and WB Panel | | | |
| IL1RA1, ADM, HIST2HAA, CD93, CA4, CYBB | | | | |
| Cluster 10 | PBMC panel | .002 | | |
| 3 genes | | | | |
| CD36, VCAN, FCGR1A | | | | |
| Cluster 11 | WB Panel | $5 \times 10^{-7}$ | | |
| 6 genes | | | | |
| IQGAP1, LTA4H, SLC16AC, CD14-2, CD14-1, CKAP4 | | | | |
| Cluster 12 | WB Panels | $5 \times 10^{-7}$ | | |
| 7 genes | | | | |
| F5, S100P, CD163, ETS2, ORM1, ARG, APLP2 | | | | |

Wilcoxon rank sum tests used for analyses,
*FDR.
**Bonferroni

Performance of a 7 Gene Cluster for Stroke Classification

The 7 transcript Cluster 1 consisted of PLBD1, PYGL, BST1, DUSP1, FOS, VCAN and FCGR1A (Table 4 and Table 5). Five of these transcripts had differed significantly between stroke and control. The upper threshold levels for each of the transcripts were based on the third quartile in the control subjects (Table 4 and FIG. 3A). Absent calls were noted for BST1 and FCGR1A in a number of the control subjects (this could reflect low or absent transcript expression). The number of subjects with elevated expression of each transcript is shown in

TABLE 5

The proportion of patients with elevated expression of between 0-7 transcripts is shown in FIG. 3B.

| Transcript | Threshold | Stroke Number of subjects with elevated transcript copy number (%) | Control Number of subjects with elevated transcript copy number (%) | p |
|---|---|---|---|---|
| PLBD1 | >0.0144 | 15/18 (83%) | 3/14 (21%) | 0.0017 |
| PYGL | >0.0115 | 13/17 (76%) | 3/12 (25%) | 0.02 |
| FOS | >0.0122 | 10/17 (59%) | 3/13 (23%) | 0.11 |
| DUSP1 | >0.0052 | 13/17 (76%) | 2/11 (18%) | 0.008 |
| BST1 | >0.0073 | 14/16 (88%) | 2/7 (28%) | 0.02 |
| VCAN | >0.0101 | 12/17 (70%) | 3/9 (33%) | 0.16 |
| FCGR1A | >0.0202 | 10/14 (71%) | 2/6 (33%) | 0.27 |
| 7 transcripts in Cluster 1 | 3 or more transcripts elevated | 15/18 (83%) | 3/15 (20%) | 0.001 |

Elevated whole blood expression of at least 3 transcripts in this 7 gene cluster classified stroke with a sensitivity of 83% and a specificity of 80% (FIG. 3B). The overall accuracy of the 7 gene classifier was high (AUC=0.854, FIG. 3C).

Performance of Three Previously Reported Transcript Panels

The Moore et al. transcripts list[4], identified in PBMCs, showed a highly significant discrimination between stroke and control (p=1.01e-9). The p values for the Tang et al. list[5] and the Barr et al. list[6], identified in whole blood, were 1.05e-5 and 0.02 respectively.

Discussion

The diagnostic utility of gene expression changes in acute ischemic stroke has been studied in a number of prior microarray studies[4-7,21,22]. However these microarray results were never validated with qPCR—the gold standard for measuring gene expression. The current study was based on three studies where gene panels had been identified using the Prediction Analysis for Microarrays[4-6] algorithm. The Grond-Ginsbach et al. study[7] was not included as only one transcript was identified and pooled samples were used.

Results from Oh et al.[21] were published after this study commenced. In several other microarray studies the utility of gene expression was investigated: for the evaluation of the risk of hemorrhagic transformation[23], defining stroke etiology[24-26] and in studying gender related gene expression changes in stroke patients[27,28].

Using HT RT-qPCR, for the first time—a new qPCR based platform that has the advantages of high accuracy and sensitivity—we have found that 40% of the transcripts were up-regulated in stroke. It is arguable as to whether corrections for multiple comparisons were needed as these transcripts were a priori specified. Nevertheless even after correction for multiple comparisons expression of a small number of transcripts were still significantly different between stroke and control. Although, the hierarchical cluster analysis was not used previously it proved to be very successful in detecting association of studied transcripts with stroke. This analysis grouped genes into 7 clusters. These clusters were highly significantly different between the stroke patients and the control subjects, with 5 remaining highly significant after stringent correction for multiple comparisons (p values as low as 7.04e-9). The cluster of 7 genes—PLBD1, PYGL, BST1, DUSP1, FOS, VCAN and FCGR1A—classified stroke with high sensitivity and specificity, respectively 80% and 83%. The similar expression of genes within a cluster in the stroke patients and control subjects, with comparable differences between two groups permitted the analysis of the expression of all genes within a cluster together. Furthermore, the quantitative information on copy number permitted threshold levels of normal and abnormal expression to be established in the control subjects.

Of interest is that while whole blood samples were used in this study, the 16 significantly altered transcripts had been identified in whole blood and in PBMCs, and that transcripts within each of the 7 identified clusters came from both whole blood and PBMC gene lists. These two cell populations overlap substantially because whole blood is composed of PBMC and polymorphonuclear leukocytes (granulocytes). Neutrophils are the main cell population within polymorphonuclear leukocytes and represent the most numerous nucleated cell fraction in whole blood, however their RNA content is almost three times lower than in PBMC[18]. The overlap between panels and detection of PBMC gene alterations in whole blood samples supports the validity of the microarray results.

Accurate and rapid stroke diagnosis is crucial for timely and effective treatment in the acute phase. Diagnosis is also necessary in subacute and delayed phase to evaluate future risks and for optimal prevention strategies. Timely diagnosis is absolutely essential for treating patients with tissue plasminogen activator—the only FDA approved treatment of ischemic stroke. However, this treatment improves the chances of recovering from stroke only if administered within 3 to 4.5 hours. Stroke diagnosis may not be conclusive in the acute phase of stroke, especially in stroke mimics, while in subacute or chronic stroke, silent stroke, inconclusive brain imaging or atypical stroke presentation may confound stroke diagnosis. Hence, additional tests, such as molecular tests, that could confirm a diagnosis of stroke, or add complementary information, are much needed.

Molecular diagnostic tests based on gene expression patterns are now available in number of diseases, including breast, colon, lung, prostate and thyroid cancers. These tests have been based on microarray identified panels and detection of overall signal intensities rather than measurements of the expression of individual genes[14,29,30]. For stroke diagnosis, methods that are highly complex, labor intensive and require expensive equipment are difficult to be applied to clinical practice and need to be available rapidly. HT RT-qPCR is very promising and can address this problem [18]. HT RT-qPCR permits absolute quantification and measuring gene expression adjusted to the input cell count, is independent of control genes. An HT RT-qPCR identified classifier may be used to develop a point-of-care system for stroke diagnosis. Until now stroke gene expression panels established in microarray studies consisted of 18 to 79 genes[4,5,22]. Clusters of 5-7 genes established using HT RT-qPCR are more feasibly applied in clinical setting, where short turnaround times and low detection limits are crucial. We have recently discussed the requirements of this system and provide a highly sensitive gene expression profiling method in Example 2 that can be measured almost in real time[15].

In summary, a proportion of previously reported genes in microarray studies in stroke were replicable using HT RT-qPCR and all except 3 were grouped together to form gene clusters highly significant for ischemic stroke detection. Grouping genes in clusters allowed the identification of gene expression classifiers that could be used in a point-of-care system. These results show the promise and potential for continuing studies of gene expression profiling in stroke and for further assessment of the sensitivity and specificity of transcript clusters for ischemic stroke detection and diagnosis. Further studies will examine the gene expression changes in terms of cellular source, time course and relation to clinical outcome.

References for Example I

[1] V. L. Feigin, M. H. Forouzanfar, R. Krishnamurthi, et al., Global and regional burden of stroke during 1990-2010: findings from the Global Burden of Disease Study 2010, Lancet. 6736 (2013) 1-11.

[2] Á. Chamorro, A. Meisel, A. M. Planas, et al., The immunology of acute stroke, Nat. Rev. Neurol. 8 (2012) 401-410.

[3] C. Iadecola, J. Anrather, The immunology of stroke: from mechanisms to translation, Nat. Med. 17 (2011) 796-808.

[4] D. F. Moore, H. Li, N. Jeffries, et al., Using peripheral blood mononuclear cells to determine a gene expression profile of acute ischemic stroke: a pilot investigation, Circulation. 111 (2005) 212-221.

[5] Y. Tang, H. Xu, X. Du, et al., Gene expression in blood changes rapidly in neutrophils and monocytes after ischemic stroke in humans: a microarray study, J. Cereb. Blood Flow Metab. 26 (2006) 1089-1102.

[6] T. L. Barr, Y. Conley, J. Ding, et al., Genomic biomarkers and cellular pathways of ischemic stroke by RNA gene expression profiling, Neurology. 75 (2010) 1009-1014.

[7] C. Grond-Ginsbach, M. Hummel, T. Wiest, et al., Gene expression in human peripheral blood mononuclear cells upon acute ischemic stroke, J. Neurol. 255 (2008) 723-731.

[8] R. L. VanGilder, J. D. Huber, C. L. Rosen, T. L. Barr, The transcriptome of cerebral ischemia, Brain Res. Bull. 88 (2012) 313-319.

[9] F. R. Sharp, G. C. Jickling, Whole genome expression of cellular response to stroke, Stroke. 44 (2013) S23-S25.

[10] A. E. Baird, Blood genomics in human stroke, Stroke. 38 (2007) 694-8.

[11] F. R. Sharp, G. C. Jickling, B. Stamova, et al., RNA expression profiles from blood for the diagnosis of stroke and its causes, J. Child Neurol. 26 (2011) 1131-1136.

[12] P. T. Nelson, D. A. Baldwin, L. M. Scearce, et al., Microarray-based, high-throughput gene expression profiling of microRNAs, Nat. Methods. 1 (2004) 155-161.

[13] E. Wang, L. D. Miller, G. A. Ohnmacht, et al., High-fidelity mRNA amplification for gene profiling, Nat. Biotechnol. 18 (2000) 457-459.

[14] S. Singhal, D. Miller, S. Ramalingam, S.-Y. Sun, Gene expression profiling of non-small cell lung cancer, Lung Cancer. 60 (2008) 313-324.

[15] Z. Peng, B. Young, A. E. Baird, S. A. Soper, Single-pair fluorescence resonance energy transfer analysis of mRNA transcripts for highly sensitive gene expression profiling in near real time, Anal. Chem. 85 (2013) 7851-7858.

[16] S. Palmer, A. P. Wiegand, F. Maldarelli, et al., New real-time reverse transcriptase-initiated PCR assay with single-copy sensitivity for human immunodeficiency virus type 1 RNA in plasma, J. Clin. Microbiol. 41 (2003) 4531-4536.

[17] A. S. Devonshire, R. Sanders, T. M. Wilkes, et al., Application of next generation qPCR and sequencing platforms to mRNA biomarker analysis, Methods. 59 (2013) 89-100.

[18] M. G. Adamski, Y. Li, E. Wagner, et al., Next-generation qPCR for the high-throughput measurement of gene expression in multiple leukocyte subsets, J. Biomol. Screen. 18 (2013) 1008-1017.

[19] S. A. Bustin, V. Benes, J. A. Garson, et al., The MIQE guidelines: minimum information for publication of quantitative real-time PCR experiments, Clin. Chem. 55 (2009) 611-622.

[20] M. G. Adamski, P. Gumann, A. E. Baird, A Method for Quantitative Analysis of Standard and High-Throughput qPCR Expression Data Based on Input Sample Quantity, PLoS One. 9 (2014) e103917.

[21] S.-H. Oh, O.-J. Kim, D.-A. Shin, et al., Alteration of immunologic responses on peripheral blood in the acute phase of ischemic stroke: blood genomic profiling study, J. Neuroimmunol. 249 (2012) 60-65.

[22] B. Stamova, H. Xu, G. Jickling, et al., Gene expression profiling of blood for the prediction of ischemic stroke, Stroke. 41 (2010) 2171-2177.

[23] G. C. Jickling, B. P. Ander, B. Stamova, et al., RNA in blood is altered prior to hemorrhagic transformation in ischemic stroke, Ann. Neurol. (2013). DOI: 10.1002/ana.23883

[24] G. C. Jickling, B. Stamova, B. P. Ander, et al., Profiles of lacunar and nonlacunar stroke, Ann. Neurol. 70 (2011) 477-485.

[25] G. C. Jickling, H. Xu, B. Stamova, et al., Signatures of cardioembolic and large-vessel ischemic stroke, Ann. Neurol. 68 (2010) 681-692.

[26] H. Xu, Y. Tang, D.-Z. Liu, et al., Gene expression in peripheral blood differs after cardioembolic compared with large-vessel atherosclerotic stroke: biomarkers for the etiology of ischemic stroke, J. Cereb. Blood Flow Metab. 28 (2008) 1320-1328.

[27] B. Stamova, Y. Tian, G. Jickling, et al., The X-chromosome has a different pattern of gene expression in women compared with men with ischemic stroke, Stroke. 43 (2012) 326-334.

[28] Y. Tian, B. Stamova, G. C. Jickling, et al., Effects of gender on gene expression in the blood of ischemic stroke patients, J. Cereb. Blood Flow Metab. 32 (2012) 780-791.

[29] E. K. Alexander, G. C. Kennedy, Z. W. Baloch, et al., Preoperative diagnosis of benign thyroid nodules with indeterminate cytology, N. Engl. J. Med. 367 (2012) 705-715.

[30] C. Sotiriou, M. J. Piccart, Taking gene-expression profiling to the clinic: when will molecular signatures become relevant to patient care?, Nat. Rev. Cancer. 7 (2007) 545-553.

Example II

A Method for Quantitative Analysis of Standard and High-Throughput qPCR Expression Data Based on Input Sample Quantity Over the past decade a rapid increase has occurred in the understanding of RNA expression and its regulation. Quantitative polymerase chain reaction(s) (qPCR) have become the gold standard for measuring gene expression. Accurate analysis of qPCR data is crucial for optimal results and a number of well-defined methods are in use to calculate gene expression. These include the comparative $C_T$ method[1], the efficiency corrected method[2] and sigmoidal curve fitting methods[3], all of which provide relative quantitative information. A standard curve of serial dilutions of a known sample is additionally required to measure the absolute number of transcript copies in a sample.

For most scientific purposes, relative quantification, expressed as fold change, is sufficient to provide the required information. Hence, the comparative $C_T$ and efficiency corrected methods, as well as the sigmoidal curve fitting methods are widely employed, but each method has strengths and weaknesses. The comparative $C_T$ method by Livak et al.[1] has the advantage of ease of use but is based on the assumption that transcript amplification efficiencies are 100%. In the efficiency corrected method by Pfaffl[2] the relative expression ratio is calculated only from the real-time PCR efficiencies and the crossing point deviation of an unknown sample versus a control. This model needs no calibration curve and gives improved quantification but is complex to use and requires determination of the amplification efficiency.

Furthermore, all of these methods require the use of reference (control or housekeeping) genes to correct for unequal amounts of biological material that may exist between the tested samples. The commonly used housekeeping genes were initially selected on the basis of their abundance and expression in a wide variety of tissues. An absolute requirement and widely held assumption of housekeeping genes has been that their expression is constant under all conditions and is unaffected by the experimental conditions[4]. However, the expression of commonly used housekeeping genes has since been found to vary considerably in many conditions[5-12]. In the case of in vitro or ex-vivo experiments it is usually possible to perform additional experiments to identify and validate appropriate control genes. In the case of clinical studies, however, where sample volumes are usually limited, it is rarely possible to test gene expression before and after the experiment (i.e., before and after the disease occurs).

The advent of next generation high throughput qPCR, based on reaction volumes scaled to the nanoliter range and with a consequent dramatic reduction in the volume of reagents and samples, has been a major advance for the analysis of clinical samples[13]. The Fluidigm Biomark system, one of the new high-throughput reverse transcription PCR (HT RT-qPCR) systems, permits up to 96 transcripts in 96 samples to be studied simultaneously during a single run, in a total of 9216 reactions. This allows many more transcripts to be studied from routine clinical samples, representing a 40 to 50 fold improvement in efficiency over standard qPCR[14,15]. However, HT RT-qPCR has also raised new issues; for example, transcript amplification efficiency may be affected by potential interactions (i.e., primer dimer, competition) between multiple primers during the preamplification and amplification steps.

In the present example, a method for the measurement of the absolute gene expression for standard and high throughput qPCR experiments based on the input sample quantity is described. Based on this method three equations were developed: (1) for the measurement of fold change differences between target and control samples; (2) for the comparison of results from different experiments and different machines after normalization to a reference cDNA sample; (3) for analyses of samples of unknown efficiency. Gene expression results calculated using the input quantity method were then validated in a serial dilution series of commercial cDNA and using different starting cell concentrations. In clinical samples, fold change values calculated with the input quantity method were compared to values obtained using other commonly used algorithms. The input quantity method has the advantages of avoiding the use of control genes, of being efficiency corrected, and providing both fold change and absolute results. This method can also be applied in the verification and quantification of qualitative results from microarray studies for multiple genes.

Requirements for the Input Quantity Method

The input quantity method has several requirements. First, the amount of material used for RNA extraction has to be measured: for example, cell count is required for cell suspensions (e.g., peripheral blood mononuclear cells (PBMCs), lymphocytes and cell lines), white blood cell (WBC) counts are needed for whole blood studies and tissue volumes are needed for solid tissues. Secondly, for reverse transcription of RNA to cDNA the same reagents, volumes and protocols for a given experiment need to be used. Thirdly, the amplification efficiency and correlation coefficients ($R^2$) should be assessed for each gene assay based on a standard dilution series. Finally, full application of this method requires the use of a standard sample (i.e., commercial cDNA—reverse transcribed cDNA from RNA extracted from all human tissues) for each measurement.

Mathematical Model for qPCR Amplification

As per Livak et al.[1], in the qPCR target cDNA sequence is amplified in an exponential fashion:

$$X_n = X_0 \times (1+E)^n \quad [1]$$

where $X_n$ is the number of target cDNA molecules after n cycles, $X_0$ is the number of cDNA molecules before amplification, E is the efficiency of target cDNA amplification and n is the number of amplification cycles. In the case of perfect efficiency (E=100%) the number of target cDNA molecules doubles every cycle.

In qPCR, the number of target cDNA molecules for a given sample is reflected by the threshold cycle—or according to the MIQE guidelines[4], quantification cycle (Cq)—because Cq is the intersection between an amplification curve and threshold. The threshold is the level of fluorescence above background fluorescence—set at the same level for all samples in the experiment. Each sample that crosses the threshold (regardless of the amplification cycle number) has the same fluorescence intensity hence the same target cDNA copy number.

$$X_{nCq} = X_0 \times (1+E)^{nCq} = K \quad [2]$$

where XnCq is the number of target cDNA molecules at the Cq, nCq is the cycle number at which amplification crosses the threshold and K is a constant value for all samples in a given experiment.

Analysis Normalized to Input Sample Quantity

In order to adjust the results of gene expression to unequal amounts of starting material the number of cells used for RNA extraction has to be incorporated into Equation 2.

$$X_0 = X_C \times CC \quad [3]$$

where Xc is the transcript number per cell and cc is the number of cells used for RNA extraction (e.g., complete blood count for whole blood analysis, or hemocytometer cell count for cell subset analysis). Hence, $$K = (X_C \times cc) \times (1+E)^{nCq} \quad [4]$$

Therefore to compare gene expression between target (T) and control (C) samples where E and K are the same for T and C, ccT is the input cell count for target sample and ccC is the cell input for the control sample. For the target samples the following formula is obtained:

$$K = (T_C \times ccT) \times (1+E)^{nCq,T} \quad [5]$$

where $T_C$ is the number of transcripts per cell in the target samples.

For the reference or control samples the following formula is obtained $$K = (C_C \times ccC) \times (1+E)^{nCq,C} \quad [6]$$

where $C_C$ is the number of transcripts per cell in the reference samples.

As K is constant, Equations 4 and 5 equal each other:

$$(T_C \times ccT) \times (1+E)^{nCq,T} = (C_C \times ccC) \times (1+E)^{nCq,C} \quad [7]$$

To obtain the comparison between target and control samples:

$$\frac{T_C}{C_C} = \frac{ccC}{ccT} \times (1+E)^{(nCq,C-nCq,T)} \quad [8]$$

This way we can obtain the measure of gene expression expressed as a fold change difference between the test and control samples.

Analysis Normalized to Input Quantity and Normalized to Standard cDNA

When a standard reference sample is introduced, for example a sample that contains a high concentration of studied transcripts, the following modifications are made, starting with Equation 2, K for sample X with a starting quantity of cc is:

$$K = (X_C \times cc) \times (1+E)^{nCq,X} \quad [9]$$

K for a standard cDNA of uniform quantity is:

$$K = cDNA_0 \times (1+E)^{nCq,cDNA} \quad [10]$$

Normalizing to cDNA:

$$(X_C \times ccX) \times (1-E)^{nCq,X} = cDNA_0 \times (1+E)^{nCq,cDNA} \quad [11]$$

$$X_C = cDNA_0 \times \frac{(1+E)^{(nCq,cDNA-nCq,X)}}{ccX} \quad [12]$$

Since the number of transcripts before amplification in standard cDNA ($cDNA_0$) is constant we may assume it is equal to 1 then:

$$X_C = \frac{(1+E)^{(nCq,cDNA-nCq,X)}}{ccX} \quad [13]$$

To obtain the comparison between test and control samples, the respective $T_c$ and $C_c$ are calculated using Equation 13. Then $T_c$ is divided by $C_c$ to obtain the measure of gene expression, expressed as a fold change.

Analysis Normalized to Input Quantity and/or Normalized to Standard cDNA without Known Efficiency If E for the working primers is not assessed in the experiment, one may make an assumption that the E equals 100%—then Equation 8 is:

$$\frac{T_0}{C_0} = \frac{cc, C}{cc, T} \times 2^{(nCq,C-nCq,T)} \quad [14]$$

Whereas, adjusting to the standard cDNA sample, for sample X Equation 12 is:

$$X_C = \frac{2^{(nCq,cDNA-nCq,X)}}{ccX} \quad [15]$$

The following materials and methods are provided to facilitate the practice of the invention described below.

To assess the reliability of the input quantity method, the stability of expression values calculated across serial dilutions of a standard cDNA sample and of different starting numbers of two samples of peripheral blood mononuclear cells (PBMCs) were determined. The validity of the input quantity method was assessed by comparison to fold changes obtained using the Livak [1] and Pfaffl [2] methods for three transcripts in a cohort of stroke patients and control subjects.

The Institutional Review Board at the State University of New York (SUNY) Downstate Medical Center approved the study. All study participants and/or authorized representatives gave full and signed informed consent. Where applicable, the conduct and reporting of the study are in accordance with the MIQE criteria[4]. The detailed laboratory protocols but not the data analysis described in this manuscript have been previously published[14].

RNA Extraction and Reverse Transcription

Whole blood was obtained from 38 ischemic stroke patients between 7 and 90 days post stroke and from 17 sex- and race-matched control subjects. RNA was extracted using column separation (All-in-One Kit; Norgen Biotek, Thorold, Ontario, Canada) from 100 μl of whole blood and from a median of 2.0 million CD4$^+$ cells. Peripheral blood mononuclear cells (PBMCs) from two control subjects were used for the cell dilution experiment, with RNA isolated from triplicate samples of 2 million, 1 million, 0.5 million and 0.25 million cells. Cellular counts (millions of cells per μl) were measured using a hemocytometer for CD4$^+$ and for PBMCs; for whole blood, the total white blood cell count was obtained from the laboratory-measured complete blood count (CBC) in each study subject.

Density gradient centrifugation with Histopaque 1077 and 1119 (Sigma-Aldrich, St. Louis, Mo.) was used to separate the PBMC fraction from the whole blood. Positive magnetic bead separation (Miltenyi Biotec, Bergisch Gladbach, Germany) was used to separate CD4$^+$ from PBMCs—the cellular purity was over 97%. The extracted RNA was resuspended in 50 μl of elution solution (All-in-One Kit protocol). cDNA was synthesized using the High Capacity cDNA Reverse Transcription Kit (Life Technologies, Carlsbad, Calif.), based on random hexamers, according to the manufacturer's protocol. Following the protocol, the proportion of RNA solution to 2×RT master mix was 1:1.

Primer Development, RT qPCR and HT-RT qPCR

The primers for qPCR were self-designed, commercially synthesized by Invitrogen and wet tested using standard RT qPCR (StepOnePlus Real-Time PCR Systems; Applied Biosystems).

Standard RT qPCR (StepOnePlus Real-Time PCR Systems; Applied Biosystems) was used to measure the expression of FDFT1 in the cell dilution experiment. Each sample and no template control were measured in triplicate. Based on a standard dilution series the efficiency for FDFT1 in this experiment was 94%.

HT RT-qPCR was run on the BioMark HD System, using 96×96 Fluidigm Dynamic Arrays (Fluidigm, South San Francisco, Calif.). HT-RT qPCR was used first, to measure the expression of FUT4, CD3E, FDFT1 and B2M in serial dilutions of commercial cDNA (Universal cDNA Reverse Transcribed by Random Hexamer: Human Normal Tissues; Biochain, Newark, Calif.) and second, to compare the expression of FDFT1, CD3E and B2M between control subjects and stroke patients in whole blood and CD4$^+$ T lymphocytes. Two 5 point, four-fold serial dilution series of commercial cDNA were run in triplicate on two different plates. The volumes of commercial cDNA (diluent) in each dilution were: 100 μl (1:1), 25 μl (1:4), 6.25 μl (1:16), 1.5625 μl (1:64) and 0.39 μl (1:256). According to the manufacturer's protocol, the assay for each HT RT-qPCR experiment contained 10 μl of cDNA. The efficiencies for the genes, assessed with HT RT-qPCR, were: B2M-87%, FDFT1-86%, FUT4-79% and CD3E-79%. Five separate gene expression plates were used in this experiment. To normalize the gene expression results for stroke and control samples from different plates, a sample of commercial cDNA (containing high concentrations of all of the transcripts studied) of standard concentration and volume was run in duplicate on each plate. Each raw gene expression result (expressed as Cq) was normalized to the average Cq value for the same gene in the commercial cDNA samples that were run on the same plate (sample Cq value for gene X was subtracted from the average commercial cDNA Cq for gene X).

Calculation of Fold Changes

Fold change differences between stroke patients and control subjects for B2M and CD3E were calculated using the input sample quantity method according to Equation 13. The relative gene expression for B2M and CD3E were measured using the comparative $C_T$ method of Livak et al.[1] and the efficiency corrected method of Pfaffl[2]. For these calculations FDFT1 was used as control gene as its expression was not different in stroke patients compared to control subjects, based on the input quantity method (p>0.05).

Statistical Analyses

The statistical analyses were performed using "R", version 2.15.2. For the cDNA dilution analysis, linear regression modeling was used. For the cell dilution series, the data were analyzed using one way ANOVA, Welch's correction for inhomogeneity of variances and post hoc t.tests with false discovery rate correction. For the analysis of the stroke versus control data, the 95% CI for the fold change values were calculated using the R package "mratios" and Dunnetts method; Wilcoxon rank sum tests were used for between group comparisons.

Figure 4:
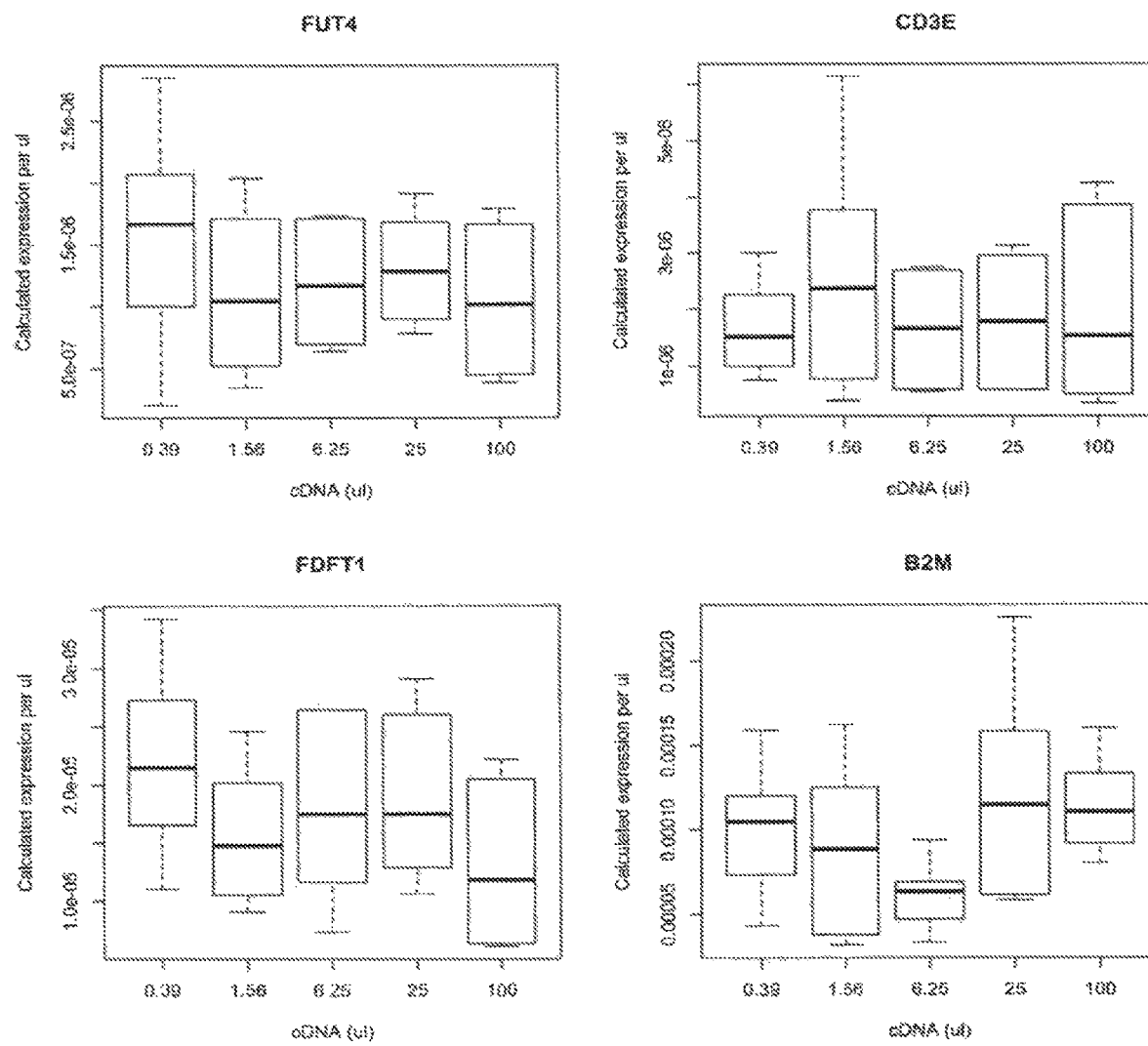
FIG. 4. Expression of FUT4, CD3E, FDFT1 and B2M in a standard dilution series of reference cDNA sample normalized to the volume of diluent using sample input quantity method.

Gene Expression Measurements Across Different Input Volumes of a Standard cDNA Sample To confirm the reliability of the sample input quantity method, the expression of 4 transcripts (FUT4, CD3E, FDFT1 and B2M) was measured in 5 point and 4-fold two serial dilutions of a standard cDNA sample. To measure the concentrations of each of the four transcripts in the standard cDNA sample, the results were normalized to the volume of diluent 100 μl (1:1), 25 μl (1:4), 6.25 μl (1:16), 1.5625 μl (1:64) and 0.39 μl (1:256). Using this normalization procedure the same expression values were expected across the range of dilutions of the standard cDNA sample. The samples were run in triplicate on two separate plates giving 6 readings per input volume. The expression of all four genes calculated with the input quantity method was stable (Table 6, FIG. 4).

TABLE 6

Expression of FUT4, CD3E, FDFT1 and B2M across serial volumes of a standard cDNA sample.

|  | FUT4 | CD3E | FDFT1 | B2M |
|---|---|---|---|---|
| Coefficient | −4.3e−8 | −6.43e−8 | −3.8e−7 | −3.3e−6 |
| P value | 0.49 | 0.65 | 0.61 | 0.48 |
| $R^2$ | −0.018 | −0.028 | −0.026 | −0.016 |

Dilution coefficient, p and $R^2$ values were obtained from linear regression analysis for each transcript Reliability of Gene Expression Measurements Across Different Starting Numbers of Cells In order to determine the influence of variables present prior to the RT qPCR step (cell counting, RNA isolation and RT PCR) the expression of FDFT1 in different starting numbers of PBMCs from two control subjects was measured. The raw data were normalized to the starting number of cells for each subject. The starting numbers of cells (2 million, 1 million, 0.5 million and 0.25 million) were within the range of the manufacturer's recommendations for RNA extraction (All-in-One Kit, Norgen Biotec).

Based on the input quantity method the expression of FDFT1 was significantly different across the input cell counts for both subjects (p=1.4e-7, Subject 1 and p=5.5e-5, Subject 2) (Table 7). Post hoc tests revealed that the expression of FDFT1 in the 0.25 million input cell count in both subjects differed significantly from the other input cell concentrations: in Subject 1 (versus 2 million, p=2.7e-6, versus 1 million, p=0.00016 and versus 0.5 million, p=7.6e-5) and in Subject 2 (versus 2 million, p=5.9e-5, versus 1 million, p=1.3e-6 and versus 0.5 million, p=1.7e-6). Comparisons between the 2 million, 1 million and 0.5 million input cell numbers were not statistically significant for both subjects (p<0.05).

TABLE 7

Expression of FDFT1 in cell dilution series

|  | 2 million cells | 1 million cells | 0.5 million cells | 0.25 million cells | p |
|---|---|---|---|---|---|
| Subject 1 | 0.26 ± 0.01 | 0.23 ± 0.02 | 0.24 ± 0.06 | 0.15 ± 0.02** | <<0.01 |
| Subject 2 | 0.049 ± 0.003 | 0.041 ± 0.005 | 0.043 ± 0.015 | 0.072 ± 0.013** | <<0.01 | p values were calculated using a one-way ANOVA.
**Post hoc tests revealed that expression of FDFT1 in the 0.25 million input cell count differed significantly from the other input cell concentrations in both subjects.

Expression of CD3E and B2M in the Late Phase of Stroke and in Control Subjects Calculated Using Three Methods To assess the validity of the input quantity method using clinical samples, the expression of CD3E and B2M in whole blood and in CD4+ T lymphocytes was compared between patients in the delayed phase of stroke and control subjects. Fold change differences in gene expression were measured using the input quantity method (normalized to cell count), and the Livak and Pfaffl methods.

By all methods B2M expression was significantly increased in whole blood in the delayed phase of stroke and CD3E was significantly increased in CD4 cells (Table 8). No alterations in the expression of CD3E were found in whole blood. A borderline increased in B2M expression in CD4 cells was found using the input quantity method.

TABLE 8

Fold change difference in the expression of B2M and CD3E in late phase stroke versus control subjects.

|  | B2M Input Quantity Method | B2M Livak | B2M Pfaffl | CD3E Input Quantity Method | CD3E Livak | CD3E Pfaffl |
|---|---|---|---|---|---|---|
| Whole blood |  |  |  |  |  |  |
| Fold Change | 2.51 | 2.19 | 2.28 | 1.27 | 1.12 | 1.22 |
| 95% CI | 1.26, 15.89 | 1.26, 5.94 | 1.32, 6.20 | 0.67, 3.34 | 0.70, 2.01 | 0.79, 2.07 |
| p | 0.017 | 0.006 | 0.003 | 0.19 | 0.48 | 0.42 |
| CD4 |  |  |  |  |  |  |
| Fold Change | 1.35 | 0.57 | 0.70 | 3.13 | 1.78 | 2.10 |
| 95% CI | 0.94, 2.17 | 0.26, 1.15 | 0.41, 1.23 | 1.61, 25.8 | 1.16, 3.42 | 1.35, 4.25 |
| p | 0.02 | 0.4999 | 0.26 | 2.10e−05 | 0.0084 | 7.50e−05 |

Discussion

Several gene expression analysis methods are in common use, but the input quantity approach presented here offers two major advantages. Firstly, this method is independent of control genes. Secondly, with the assumptions of 1) uniform efficiency of RNA extraction and RT qPCR and 2) a constant concentration and volume of a standard sample, this method permits absolute quantification, expressed as the fraction of transcripts in the standard sample, across different experiments. The proposed algorithm is efficiency corrected, although analysis of results without known efficiency is also possible. With the use of a standard sample, the input quantity method also permits the comparison and analysis of results from different batches and results acquired on different qPCR machines. Furthermore, with the advent of HT RT-qPCR, this analytical method is also very useful for clinical research, where sample volumes are limited.

Our analyses show that the sample input quantity method permits gene expression to be measured across a wide range of commercial cDNA. Although the performance of both RNA extraction and RT qPCR may differ significantly across different cell concentrations and kits[15], our results show that, using the same protocol and reagents within the input quantities we tested, these variables can be successfully controlled. Furthermore, the expression of B2M and CD3E in study subjects calculated using three methods was highly concordant.

The rationale for the use of housekeeping (or control or reference genes) is to correct gene expression results, reflected as differences in Cq values between target and control samples, that could result from two main factors: different amounts of starting material or different levels of expression. Traditionally, housekeeping genes have been chosen on the basis of their abundance, ubiquitous expression across tissues and the assumption that their expression is stable under physiological and experimental conditions. However, the expression of conventionally used housekeeping genes varies considerably in many conditions. Therefore, reference gene selection requires additional experiments to validate gene expression stability under different experimental conditions[6-12,14]. In many conditions, especially in the clinical setting, it is not possible to measure the effect of the disease/condition on reference gene expression.

The algorithm used for our sample input quantity method employs normalization to the sample input quantity (cell count, tissue volume etc.), which in result permits an absolute gene expression analysis. This method varies from the relative analysis approach, where results are normalized to reference gene expression. Due to normalization to the input quantity (measured in absolute scale) the measure of gene expression remains absolute, as in our method. In contrast, the gene expression from the relative analysis approach is based on the normalization to reference gene expression. Thus the ratio of the target gene expression to the reference gene expression represents a relative measure. By introducing a standard sample (of a stable transcript concentration), our method allows us to compare gene expression between different experiments. Instead of directly measuring transcript copy number—as it is commonly done in absolute measurements of gene expression—in our method, the measured gene expression is presented as a fraction of transcripts present in the standard sample. This fraction can be converted to the transcript copy number by measuring concentration of the target gene in the standard sample.

The input quantity approach presented here can be applied to clinical studies, to verify and quantitate microarray results, and to large scale studies of gene or microRNA expression. Having knowledge of the input cell count for all samples and the use of a uniform standard, first, allows normalization to the amount of starting material, and second, the use of the same standard allows normalization of results between different laboratories and different equipment.

References for Example II

1. Livak K J, Schmittgen T D (2001) Analysis of relative gene expression data using real-time quantitative PCR and the 2(-Delta Delta C(T)) Method. Methods 25: 402-408.
2. Pfaffl M W (2001) A new mathematical model for relative quantification in real-time RT-PCR. Nucleic Acids Res 29: e45.
3. Liu M, Udhe-Stone C, Goudar C T (2011) Progress curve analysis of qRT-PCR reactions using the logistic growth equation. Biotechnol Prog 27: 1407-1414.
4. Bustin S a, Benes V, Garson J a, Hellemans J, Huggett J, et al. (2009) The MIQE guidelines: minimum information for publication of quantitative real-time PCR experiments. Clin Chem 55: 611-622.
5. Dheda K, Huggett J F, Bustin S a, Johnson M a, Rook G, et al. (2004) Validation of housekeeping genes for normalizing RNA expression in real-time PCR. Biotechniques 37: 112-119.
6. Vandesompele J, De Preter K, Pattyn F, Poppe B, Van Roy N, et al. (2002) Accurate normalization of real-time quantitative RT-PCR data by geometric averaging of multiple internal control genes. Genome Biol 3: RESEARCH0034.
7. Chang T J, Juan C C, Yin P H, Chi C W, Tsay H J (1998) Up-regulation of beta-actin, cyclophilin and GAPDH in NIS1 rat hepatoma. Oncol Rep 5: 469-471.
8. Feroze-Merzoug F, Berquin I M, Dey J, Chen Y Q (2002) Peptidylprolyl isomerase A (PPIA) as a preferred internal control over GAPDH and beta-actin in quantitative RNA analyses. Biotechniques 32: 776-782.
9. Nishimura M, Nikawa T, Kawano Y, Nakayama M, Ikeda M (2008) Effects of dimethyl sulfoxide and dexamethasone on mRNA expression of housekeeping genes in cultures of C2C12 myotubes. Biochem Biophys Res Commun 367: 603-608.
10. Lin J, Redies C (2012) Histological evidence: housekeeping genes beta-actin and GAPDH are of limited value for normalization of gene expression. Dev Genes Evol 222: 369-376.
11. Sikand K, Singh J, Ebron J S, Shukla G C (2012) Housekeeping gene selection advisory: glyceraldehyde-3-phosphate dehydrogenase (GAPDH) and β-actin are targets of miR-644a. PLoS One 7: e47510.
12. Li R, Shen Y (2013) An old method facing a new challenge: re-visiting housekeeping proteins as internal reference control for neuroscience research. Life Sci 92: 747-751.
13. Devonshire A S, Sanders R, Wilkes T M, Taylor M S, Foy C a, et al. (2013) Application of next generation qPCR and sequencing platforms to mRNA biomarker analysis. Methods 59: 89-100.
14. Adamski M G, Li Y, Wagner E, Yu H, Seales-Bailey C, et al. (2013) Next-generation qPCR for the high-throughput measurement of gene expression in multiple leukocyte subsets. J Biomol Screen 18: 1008-1017.
15. Spurgeon S L, Jones R C, Ramakrishnan R (2008) High throughput gene expression measurement with real time PCR in a microfluidic dynamic array. PLoS One 3: e1662.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for detecting a cluster of nucleic acid transcripts in a human patient, comprising:
   a) obtaining a whole blood sample from said patient,
   b) detecting in the sample, said cluster consisting of transcripts of each of PLBD1, FOS, DUSP1, VCAN, BST1, FCGR1A, and PYGL by reverse transcribing RNA transcripts extracted from said sample into cDNA and amplifying said cDNA using primer pairs and performance of quantitative polymerase chain reaction (qPCR) thereby detecting and quantifying nucleic acids encoding PLBD1, FOS, DUSP1, VCAN, BST1, FCGR1A, and PYGL in said whole blood sample, wherein said primer pairs are selected from SEQ ID NO: 24 and SEQ ID NO: 64, SEQ ID NO: 16 and SEQ ID NO: 56, SEQ ID NO: 10 and SEQ ID NO: 50, SEQ ID NO: 6 and SEQ ID NO: 46, SEQ ID NO: 18 and SEQ ID NO: 58, SEQ ID NO: 21 and SEQ ID NO: 61 and SEQ ID NO: 37 and SEQ ID NO: 27.

2. A method for treating a human stroke patient, comprising:
   a) obtaining a whole blood sample from said patient;
   b) detecting in the sample, a cluster of nucleic acids consisting of transcripts of each of PLBD1, FOS, DUSP1, VCAN, BST1, FCGR1A, and PYGL by reverse transcribing RNA transcripts extracted from said sample into cDNA and amplifying said cDNA using primer pairs and performance of quantitative polymerase chain reaction (qPCR) thereby detecting and quantifying transcripts encoding PLBD1, FOS, DUSP1, VCAN, BST1, FCGR1A, and PYGL in said whole blood sample, and
   c) administering an agent useful for the amelioration of stroke symptoms to said stroke patient, wherein said primer pairs are selected from SEQ ID NO: 24 and SEQ ID NO: 64, SEQ ID NO: 16 and SEQ ID NO: 56, SEQ ID NO: 10 and SEQ ID NO: 50, SEQ ID NO: 6 and SEQ ID NO: 46, SEQ ID NO: 18 and SEQ ID NO: 58, SEQ ID NO: 21 and SEQ ID NO: 61 and SEQ ID NO: 37 and SEQ ID NO: 27.

* * * * *

SEQUENCE LISTING

<160> NUMBER OF SEQ ID NOS: 80

<210> SEQ ID NO 1
<211> LENGTH: 21
<212> TYPE: DNA
<213> ORGANISM: Artificial Sequence
<220> FEATURE:

```
<223> OTHER INFORMATION: primer

<400> SEQUENCE: 1
aaatcccatg agtttcacgc c                                              21

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ctcggctttg acagagtgca agac                                           24

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gccacaacag gtcgctcatc cc                                             22

<210> SEQ ID NO 4
<211> LENGTH: 21
<212> TYPE: DNA
<213> ORGANISM: Artificial Sequence
<220> FEATURE:
<223> OTHER INFORMATION: primer

<400> SEQUENCE: 4
gctgctcggc gttctctcag g                                              21

<210> SEQ ID NO 5
<211> LENGTH: 24
<212> TYPE: DNA
<213> ORGANISM: Artificial Sequence
<220> FEATURE:
<223> OTHER INFORMATION: primer

<400> SEQUENCE: 5
gcatgcggtt gctcaggatg gaaa                                           24

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
aaacgacctg atcgctgcaa aatga                                          25

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
ccccttggtg ccaacagatg agg                                            23
```

```
<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
ggtgccaaca gatgaggttc aca                                              23

<210> SEQ ID NO 9
<211> LENGTH: 22
<212> TYPE: DNA
<213> ORGANISM: Artificial Sequence
<220> FEATURE:
<223> OTHER INFORMATION: primer

<400> SEQUENCE: 9
cttagcaggg tctgcgcttc gc                                               22

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tacgatcagg gtggcccggt g                                                21

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
tccagtgcgt gctgctcaac aa                                               22

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12
gggcacctct tccattgggg c                                                21

<210> SEQ ID NO 13
<211> LENGTH: 25
<212> TYPE: DNA
<213> ORGANISM: Artificial Sequence
<220> FEATURE:
<223> OTHER INFORMATION: primer

<400> SEQUENCE: 13
tcagcaaatg caaagaaggg agacc                                            25

<210> SEQ ID NO 14
<211> LENGTH: 20
<212> TYPE: DNA
<213> ORGANISM: Artificial Sequence
<220> FEATURE:
<223> OTHER INFORMATION: primer
```

<400> SEQUENCE: 14
actggccccg ggaatcagct                                              20

<210> SEQ ID NO 15
<211> LENGTH: 21
<212> TYPE: DNA
<213> ORGANISM: Artificial Sequence
<220> FEATURE:
<223> OTHER INFORMATION: primer

<400> SEQUENCE: 15
ggccggctac atcgaggctc t                                            21

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cccctccgct ggggcttact                                              20

<210> SEQ ID NO 17
<211> LENGTH: 23
<212> TYPE: DNA
<213> ORGANISM: Artificial Sequence
<220> FEATURE:
<223> OTHER INFORMATION: primer

<400> SEQUENCE: 17
gcgcctacgg aaactcagcc acc                                          23

<210> SEQ ID NO 18
<211> LENGTH: 22
<212> TYPE: DNA
<213> ORGANISM: Artificial Sequence
<220> FEATURE:
<223> OTHER INFORMATION: primer

<400> SEQUENCE: 18
tgagtcccga gcagcggaac aa                                           22

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tggcaggctg ggtccctctc                                              20

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
aaactctcca tcacccaggg tcag                                         24

<210> SEQ ID NO 21
<211> LENGTH: 23

<212> TYPE: DNA
<213> ORGANISM: Artificial Sequence
<220> FEATURE:
<223> OTHER INFORMATION: primer

<400> SEQUENCE: 21
gcaagtggac accacaaagg cag                                    23

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
ctggccggct tcacaggaag t                                      21

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
ccgcgctcgg ggctctaaga g                                      21

<210> SEQ ID NO 24
<211> LENGTH: 24
<212> TYPE: DNA
<213> ORGANISM: Artificial Sequence
<220> FEATURE:
<223> OTHER INFORMATION: primer

<400> SEQUENCE: 24
gggttacctc actgccccac acat                                   24

<210> SEQ ID NO 25
<211> LENGTH: 25
<212> TYPE: DNA
<213> ORGANISM: Artificial Sequence
<220> FEATURE:
<223> OTHER INFORMATION: primer

<400> SEQUENCE: 25
cgagcagaag gtgcagtctt tgcaa                                  25

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
gggccgctcc tactctgcct                                        20

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
cgatattcgg gcagcgaggg c          21

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
cctgaacctg gccgtggctg            20

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
ttgaggggtt aacattaggc tggga       25

<210> SEQ ID NO 30
<211> LENGTH: 23
<212> TYPE: DNA
<213> ORGANISM: Artificial Sequence
<220> FEATURE:
<223> OTHER INFORMATION: primer

<400> SEQUENCE: 30 gccctgaac cccagaacaa cca         23

<210> SEQ ID NO 31
<211> LENGTH: 23
<212> TYPE: DNA
<213> ORGANISM: Artificial Sequence
<220> FEATURE:
<223> OTHER INFORMATION: primer

<400> SEQUENCE: 31
ggcggagacc acagtttggc aat         23

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tcggccagtg cagagtcaca c          21

<210> SEQ ID NO 33
<211> LENGTH: 24
<212> TYPE: DNA
<213> ORGANISM: Artificial Sequence
<220> FEATURE:
<223> OTHER INFORMATION: primer

<400> SEQUENCE: 33
gagctctgaa gggagagact gtga        24

<210> SEQ ID NO 34
<211> LENGTH: 20
<212> TYPE: DNA
<213> ORGANISM: Artificial Sequence

```
<220> FEATURE:
<223> OTHER INFORMATION: primer

<400> SEQUENCE: 34
ggaccgcccc ttgcaggttt                                                   20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
ttcccgatcg ccaggcagga                                                   20

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
gaagtgcacg tcctgcggct                                                   20

<210> SEQ ID NO 37
<211> LENGTH: 22
<212> TYPE: DNA
<213> ORGANISM: Artificial Sequence
<220> FEATURE:
<223> OTHER INFORMATION: primer

<400> SEQUENCE: 37
ctacgacaag tgccccaagc tt                                                22

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
tccccagaca ggggtagtgc g                                                 21

<210> SEQ ID NO 39
<211> LENGTH: 20
<212> TYPE: DNA
<213> ORGANISM: Artificial Sequence
<220> FEATURE:
<223> OTHER INFORMATION: primer

<400> SEQUENCE: 39
cgcgcctcca aggtttcacg                                                   20

<210> SEQ ID NO 40
<211> LENGTH: 23
<212> TYPE: DNA
<213> ORGANISM: Artificial Sequence
<220> FEATURE:
<223> OTHER INFORMATION: primer

<400> SEQUENCE: 40
ccagatacgt gggaggccaa gag                                               23
```

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
cagaccccta actggtgctg tt                                              22

<210> SEQ ID NO 42
<211> LENGTH: 21
<212> TYPE: DNA
<213> ORGANISM: Artificial Sequence
<220> FEATURE:
<223> OTHER INFORMATION: primer

<400> SEQUENCE: 42
tccccgaggc ctggcttatg g                                               21

<210> SEQ ID NO 43
<211> LENGTH: 24
<212> TYPE: DNA
<213> ORGANISM: Artificial Sequence
<220> FEATURE:
<223> OTHER INFORMATION: primer

<400> SEQUENCE: 43
ggctcagaat ggcctccttt tcca                                            24

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
tgtccagtgc ttcaacccac aact                                            24

<210> SEQ ID NO 45
<211> LENGTH: 21
<212> TYPE: DNA
<213> ORGANISM: Artificial Sequence
<220> FEATURE:
<223> OTHER INFORMATION: primer

<400> SEQUENCE: 45
ggctccccca aggtccaaag c                                               21

<210> SEQ ID NO 46
<211> LENGTH: 21
<212> TYPE: DNA
<213> ORGANISM: Artificial Sequence
<220> FEATURE:
<223> OTHER INFORMATION: primer

<400> SEQUENCE: 46
ggccgcaagc gactgttcct t                                               21

<210> SEQ ID NO 47
<211> LENGTH: 24
<212> TYPE: DNA
<213> ORGANISM: Artificial Sequence
<220> FEATURE:
<223> OTHER INFORMATION: primer -continued

```
<400> SEQUENCE: 47
cggctgcctc ttatatccca gaga                                          24

<210> SEQ ID NO 48
<211> LENGTH: 23
<212> TYPE: DNA
<213> ORGANISM: Artificial Sequence
<220> FEATURE:
<223> OTHER INFORMATION: primer

<400> SEQUENCE: 48
agccagcccc cttcctttcc tta                                           23

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
cgagcggtgt cagcgcctag                                               20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
aggtgcctcg gtcgagcaca                                               20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
tctgcggtct gcccacgtac                                               20

<210> SEQ ID NO 52
<211> LENGTH: 21
<212> TYPE: DNA
<213> ORGANISM: Artificial Sequence
<220> FEATURE:
<223> OTHER INFORMATION: primer

<400> SEQUENCE: 52
gcagagccgc agccatctga a                                             21

<210> SEQ ID NO 53
<211> LENGTH: 23
<212> TYPE: DNA
<213> ORGANISM: Artificial Sequence
<220> FEATURE:
<223> OTHER INFORMATION: primer

<400> SEQUENCE: 53
gaggatgaca ggaatgcagg gcc                                           23

<210> SEQ ID NO 54
```

```
<211> LENGTH: 22
<212> TYPE: DNA
<213> ORGANISM: Artificial Sequence
<220> FEATURE:
<223> OTHER INFORMATION: primer

<400> SEQUENCE: 54
tcaccctgtg ccatttctgg ca                                              22

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
ccgtgtgcca gtgctggtga                                                 20

<210> SEQ ID NO 56
<211> LENGTH: 22
<212> TYPE: DNA
<213> ORGANISM: Artificial Sequence
<220> FEATURE:
<223> OTHER INFORMATION: primer

<400> SEQUENCE: 56
ggtctgtctc cgcttggagt gt                                              22

<210> SEQ ID NO 57
<211> LENGTH: 22
<212> TYPE: DNA
<213> ORGANISM: Artificial Sequence
<220> FEATURE:
<223> OTHER INFORMATION: primer

<400> SEQUENCE: 57
tggtgctaca ctgggacccc ac                                              22

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
gctgccttcc ccgcaggatt                                                 20

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
tccccatggc cctggcttgt                                                 20

<210> SEQ ID NO 60
<211> LENGTH: 22
<212> TYPE: DNA
<213> ORGANISM: Artificial Sequence
<220> FEATURE:
<223> OTHER INFORMATION: primer

<400> SEQUENCE: 60
```
agctggagag ggcaagggaa gc                                          22

<210> SEQ ID NO 61
<211> LENGTH: 22
<212> TYPE: DNA
<213> ORGANISM: Artificial Sequence
<220> FEATURE:
<223> OTHER INFORMATION: primer

<400> SEQUENCE: 61
accaggcctc tgcaagagca ac                                          22

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
tggtcccggc gacctcagtc                                             20

<210> SEQ ID NO 63
<211> LENGTH: 25
<212> TYPE: DNA
<213> ORGANISM: Artificial Sequence
<220> FEATURE:
<223> OTHER INFORMATION: primer

<400> SEQUENCE: 63
ggtggtttct tgcttgggtc taggg                                       25

<210> SEQ ID NO 64
<211> LENGTH: 22
<212> TYPE: DNA
<213> ORGANISM: Artificial Sequence
<220> FEATURE:
<223> OTHER INFORMATION: primer

<400> SEQUENCE: 64
gcggagcaat gtcccatgtc cc                                          22

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
agccgctcct ccaccgtgtt                                             20

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
accgtcgagt cagctcgggt                                             20

<210> SEQ ID NO 67
<211> LENGTH: 24
<212> TYPE: DNA

<213> ORGANISM: Artificial Sequence
<220> FEATURE:
<223> OTHER INFORMATION: primer

<400> SEQUENCE: 67
cttttccact ctgcaggaag cctg                                              24

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
cggtgcggtg gttctgggtc                                                   20

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
gcagccttca gcgcaatggc                                                   20

<210> SEQ ID NO 70
<211> LENGTH: 23
<212> TYPE: DNA
<213> ORGANISM: Artificial Sequence
<220> FEATURE:
<223> OTHER INFORMATION: primer

<400> SEQUENCE: 70
accatgtttc ccagtctccg cgc                                               23

<210> SEQ ID NO 71
<211> LENGTH: 21
<212> TYPE: DNA
<213> ORGANISM: Artificial Sequence
<220> FEATURE:
<223> OTHER INFORMATION: primer

<400> SEQUENCE: 71
gacctcccac gactggtgtg c                                                 21

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
gggggactgg cggtccttct                                                   20

<210> SEQ ID NO 73
<211> LENGTH: 24
<212> TYPE: DNA
<213> ORGANISM: Artificial Sequence
<220> FEATURE:
<223> OTHER INFORMATION: primer

<400> SEQUENCE: 73
aagagcattt cttctgggct ccca                                              24

```
<210> SEQ ID NO 74
<211> LENGTH: 20
<212> TYPE: DNA
<213> ORGANISM: Artificial Sequence
<220> FEATURE:
<223> OTHER INFORMATION: primer

<400> SEQUENCE: 74
caccagggcg aggcacacag                                           20

<210> SEQ ID NO 75
<211> LENGTH: 20
<212> TYPE: DNA
<213> ORGANISM: Artificial Sequence
<220> FEATURE:
<223> OTHER INFORMATION: primer

<400> SEQUENCE: 75
ttgcctttgc gcagcaagcg                                           20

<210> SEQ ID NO 76
<211> LENGTH: 24
<212> TYPE: DNA
<213> ORGANISM: Artificial Sequence
<220> FEATURE:
<223> OTHER INFORMATION: primer

<400> SEQUENCE: 76
gcaacgatag ggtttctcac caca                                      24

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
gctggatggc cacctgatcc g                                         21

<210> SEQ ID NO 78
<211> LENGTH: 25
<212> TYPE: DNA
<213> ORGANISM: Artificial Sequence
<220> FEATURE:
<223> OTHER INFORMATION: primer

<400> SEQUENCE: 78
cattggtttc cccaggtcca tgacg                                     25

<210> SEQ ID NO 79
<211> LENGTH: 23
<212> TYPE: DNA
<213> ORGANISM: Artificial Sequence
<220> FEATURE:
<223> OTHER INFORMATION: primer

<400> SEQUENCE: 79
tccaggacag agccatagtg cgg                                       23

<210> SEQ ID NO 80
<211> LENGTH: 24
<212> TYPE: DNA
<213> ORGANISM: Artificial Sequence
<220> FEATURE:
```

```
<223> OTHER INFORMATION: primer

<400> SEQUENCE: 80
gcccccagtt cttctcatcg ttca                                              24
```